(12) United States Patent
Hoffmann et al.

(10) Patent No.: US 10,345,309 B2
(45) Date of Patent: Jul. 9, 2019

(54) BIOMARKERS FOR GASTRIC CANCER AND USES THEREOF

(71) Applicant: Adelaide Research & Innovation Pty Ltd, Adelaide (AU)

(72) Inventors: Peter Hoffmann, Largs North (AU); Megan Penno, Mile End (AU); Matthias Robert Walter Ernst, Victoria (AU)

(73) Assignee: Adelaide Research & Innovation Pty Ltd, Adelaide (AU)

( * ) Notice: Subject to any disclaimer, the term of this patent is extended or adjusted under 35 U.S.C. 154(b) by 99 days.

(21) Appl. No.: 15/158,146

(22) Filed: May 18, 2016

(65) Prior Publication Data

US 2016/0370373 A1   Dec. 22, 2016

Related U.S. Application Data

(63) Continuation of application No. 14/373,332, filed as application No. PCT/AU2013/000030 on Jan. 17, 2013, now abandoned.

(30) Foreign Application Priority Data

Jan. 20, 2012   (AU) ................................. 2012900233

(51) Int. Cl.
   *G01N 33/574*   (2006.01)
   *G01N 33/50*   (2006.01)
   *C12Q 1/6886*   (2018.01)
   *G01N 33/92*   (2006.01)

(52) U.S. Cl.
   CPC ..... *G01N 33/57446* (2013.01); *C12Q 1/6886* (2013.01); *G01N 33/5023* (2013.01); *G01N 33/57488* (2013.01); *G01N 33/92* (2013.01); *C12Q 2600/112* (2013.01); *C12Q 2600/136* (2013.01); *C12Q 2600/158* (2013.01); *C12Q 2600/16* (2013.01); *G01N 2333/65* (2013.01); *G01N 2333/76* (2013.01); *G01N 2333/775* (2013.01); *G01N 2333/811* (2013.01); *G01N 2800/52* (2013.01); *G01N 2800/60* (2013.01)

(58) Field of Classification Search
   None
   See application file for complete search history.

(56) References Cited

U.S. PATENT DOCUMENTS

2009/0018026 A1   1/2009   Kim et al.
2013/0071857 A1*  3/2013   Lo .................... G01N 33/57446
                                                    435/7.9

FOREIGN PATENT DOCUMENTS

JP   2008-263840   11/2008
WO   WO 2007/100183   9/2007
WO   WO 2011/097960   8/2011

OTHER PUBLICATIONS

Ahn et al., "Serum biomarker panels for the diagnosis of gastric adenocarcinoma" Br. J. Cancer, vol. 106, No. 4, pp. 733-739, 2012.
Bi et al., "Overexpression of clusterin correlates with tumor progression, metastasis in gastric cancer: a study on tissue microarrays," Neoplasma, vol. 57, No. 3, pp. 191-197, 2010.
Bones et al., "Glycomic and glycoproteomic analysis of serum from patients with stomach cancer reveals potential markers arising from host defense response mechanisms," J. Proteome Res., vol. 10, pp. 1246-1265, 2011.
Chong et al., "ITIH3 is a potential biomarker for early detection of gastric cancer," J. Proteome Res., vol. 9, No. 7, pp. 3671-3679, 2010.
Li et al., "Over-expression of Ephb4 is associated with carcinogenesis of gastric cancer," Dig. Dis. Sci., vol. 56, No. 3, pp. 698-706, 2011.
Liu et al., "Proteomic identification of serum biomarkers for gastric cancer using multidimensional liquid chromatography and 2D differential gel electrophoresis," Clin. Chim. Acta, vol. 413, No. 13-14, pp. 1098-1106, 2012.
Mucci et al., "Plasma levels of acid-labile subunit, free insulin-like growth factor-I, and prostate cancer risk: a prospective study," Cancer Epidemiol. Biomarkers Prev., vol. 19, No. 2, pp. 484-491, 2010.
Penno et al., "2D-DIGE analysis of sera from transgenic mouse models reveals novel candidate Protein biomarkers for human gastric cancer," J. Proteomics, vol. 77, pp. 40-58, 2012.
Rajkumar et al., "Identification and validation of genes involved in gastric tumorigenesis," Cancer Cell International, 10:45, 2010 (12 pages).
Supplementary European Search Report for EP 13 73 8133, completed Jul. 15, 2015, 4 pages.
Teramoto et al., "Prediction of lymphatic invasion/lymph node metastasis, recurrence, and survival in patients with gastric cancer by cDNA array-based expression profiling," J. Surg. Res., vol. 124, No. 2, pp. 225-236, 2005.
Tockman et al., "Considerations in bringing a cancer biomarker to clinical application," Cancer Res., vol. 52, pp. 2711s-2718s, 1992.

* cited by examiner

Primary Examiner — Mark Halvorson
(74) Attorney, Agent, or Firm — Klarquist Sparkman, LLP

(57) ABSTRACT

The present invention provides biological markers associated with gastric cancer. In particular, the present invention provides a method of diagnosing gastric cancer (GC) in a subject, the method including: measuring an expression level of one or more proteins in the subject, wherein the one or more proteins are selected from the group consisting of vitamin D binding protein (VDBP), clusterin, insulin like growth factor binding protein complex acid labile subunit (IGFALS), and afamin; comparing the expression level of the or each protein in the subject to a reference expression level for the or each protein; and diagnosing GC in the subject on the basis of the comparison. On the basis of the identification of biological markers associated with gastric cancer, the present invention also provides a method of determining if a subject is susceptible to developing gastric cancer, a method of assessing progression of gastric cancer in a subject, a method for screening a candidate therapeutic agent useful for treating gastric cancer in a subject, and a kit for diagnosing gastric cancer in a subject.

4 Claims, 21 Drawing Sheets

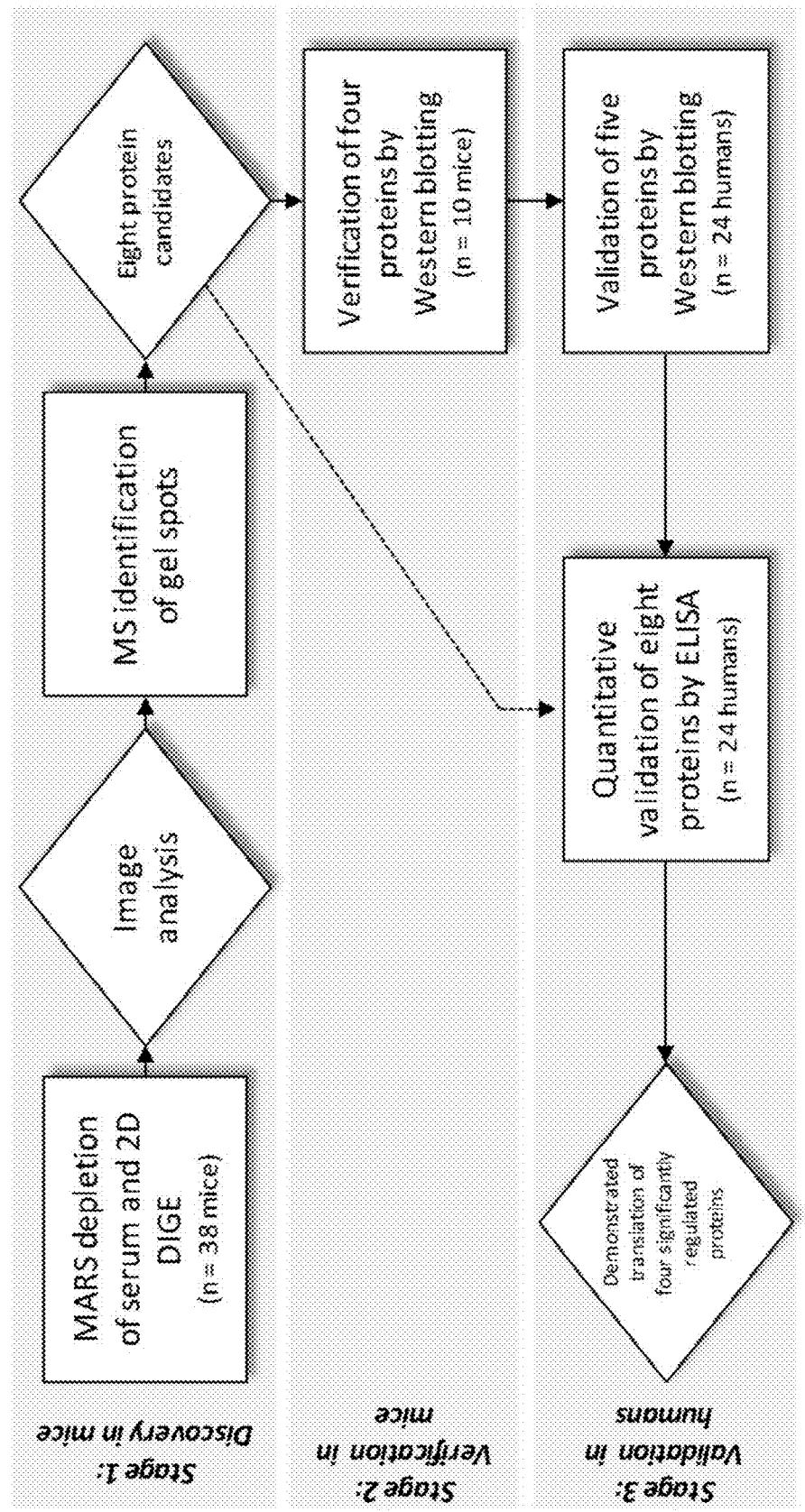

FIG. 3

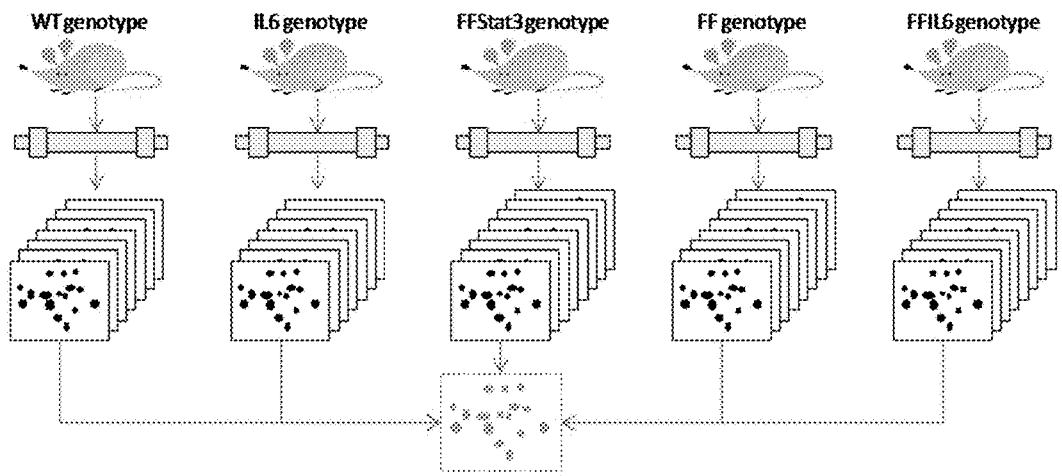

1. Matching to master gel in DeCyder, 512 spots matched to >70% spot maps (≥27/38)

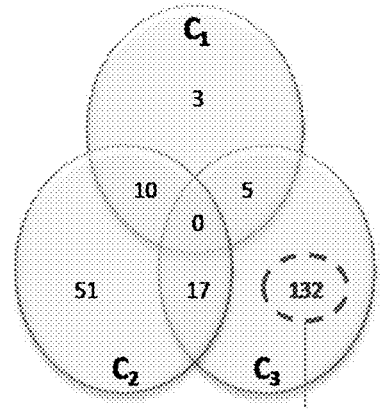

2. Three comparisons of 512 matched spot volumes involving different genotypes to identify and eliminate those spots regulated in association with the IL6 knockout and the systemic inflammatory response versus those specifically regulated in GC, revealing 132 spots of interest.

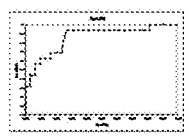

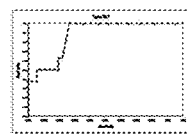

4. Elimination of FF mutation associated spots in $ROC_2$ ($AUC_2 > AUC_1$) revealing 112 spots of interest 3. Elimination of inadequate discriminators of GC versus non-GC in $ROC_1$ ($AUC_1 < 0.85$) revealing 123 spots of interest

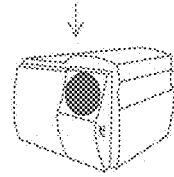

5. MS analysis of 112 spots, identifying 31 murine proteins corresponding to 28 human homologues

6. Selection of a subset of eight candidate biomarkers for follow-up verification in mice and validation in human sera.

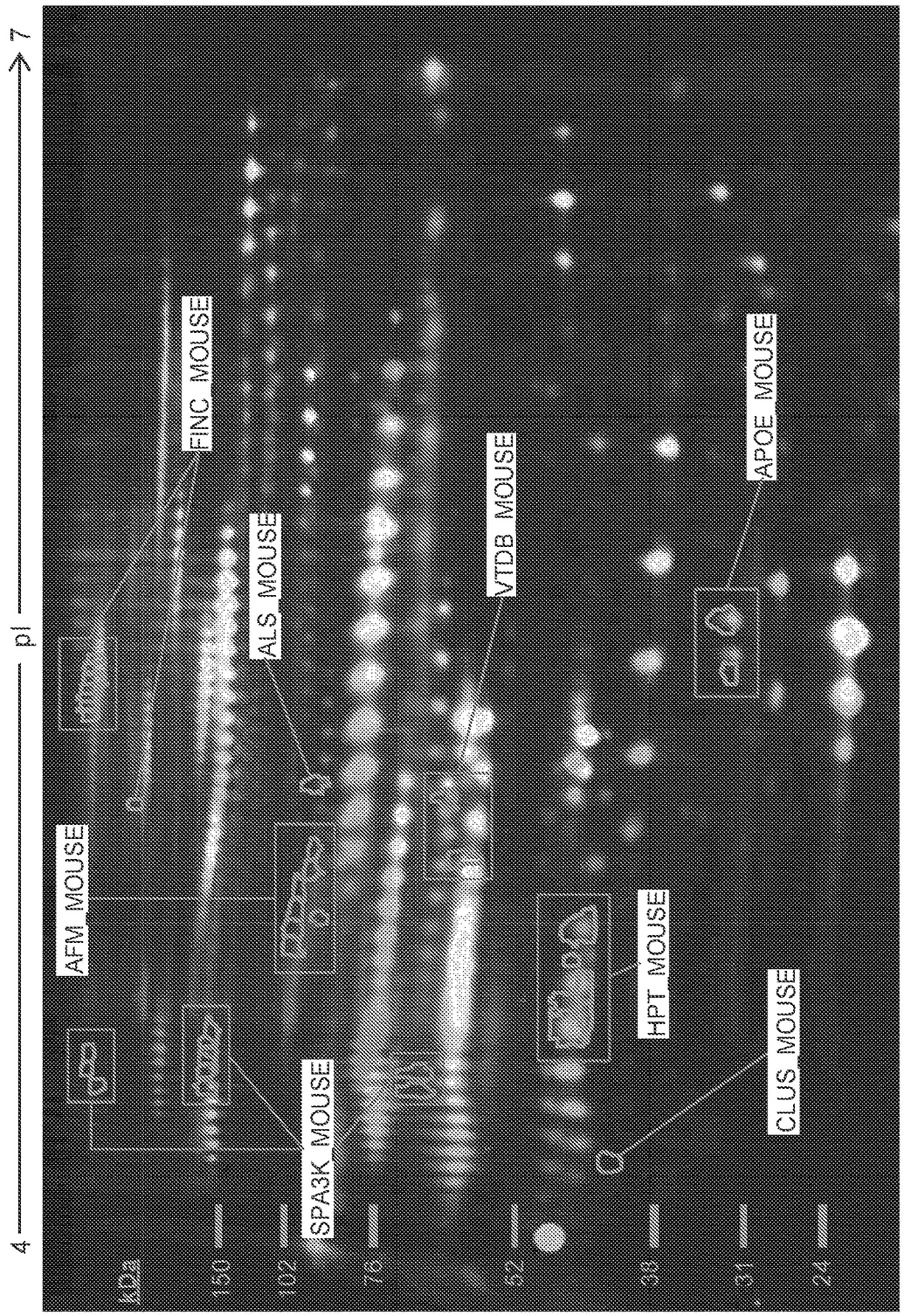

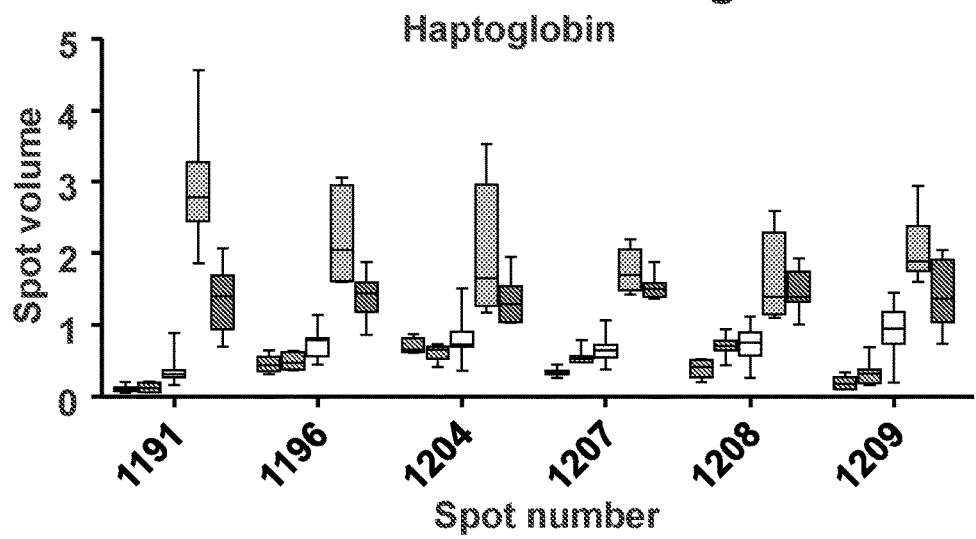
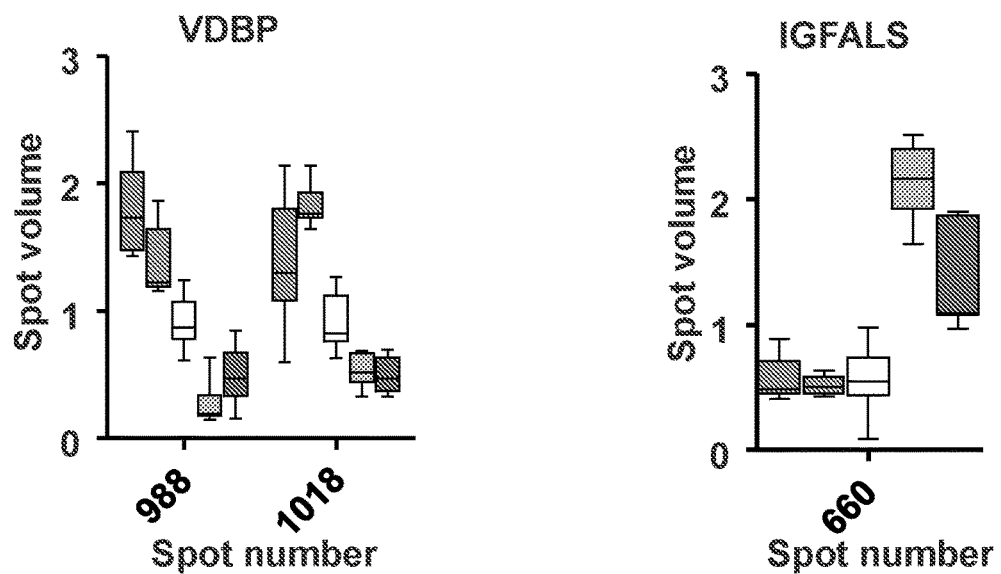
Figure 5B continued

FIG. 11
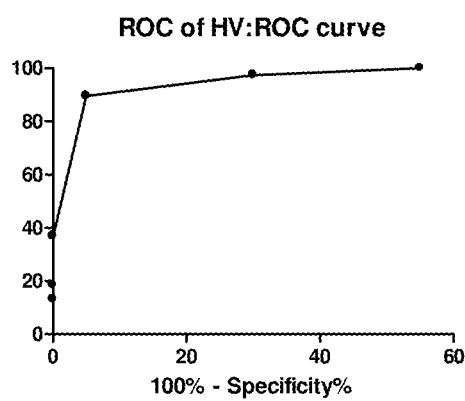
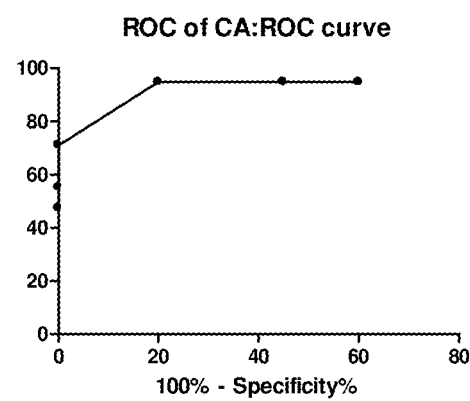
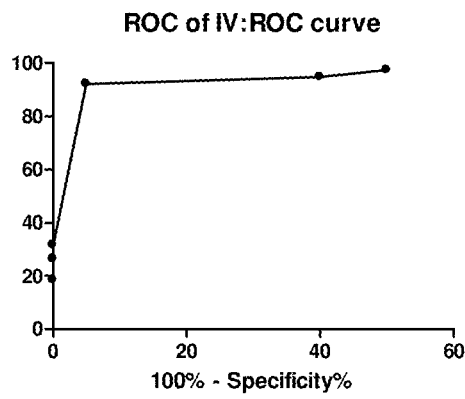
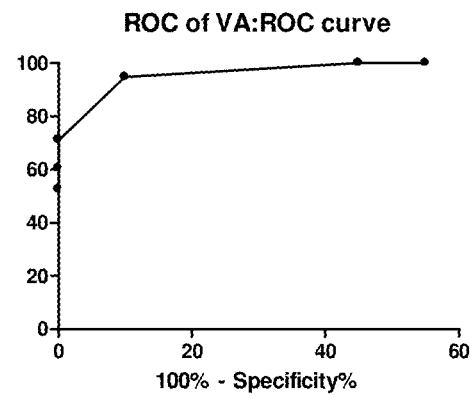
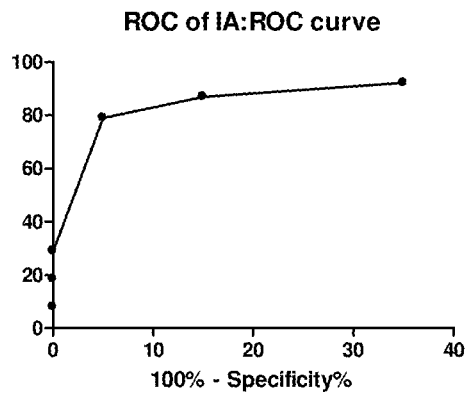

FIG. 12
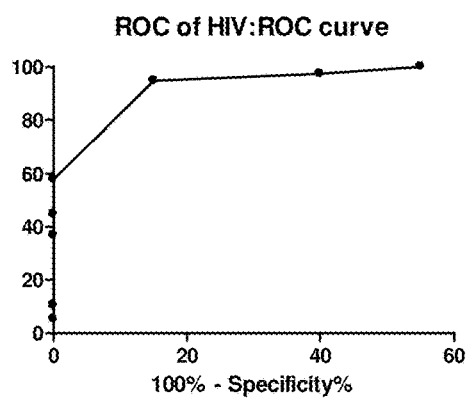
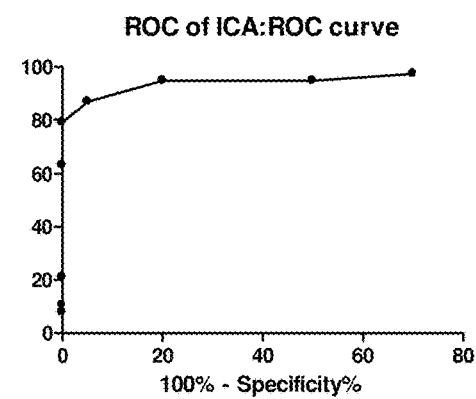
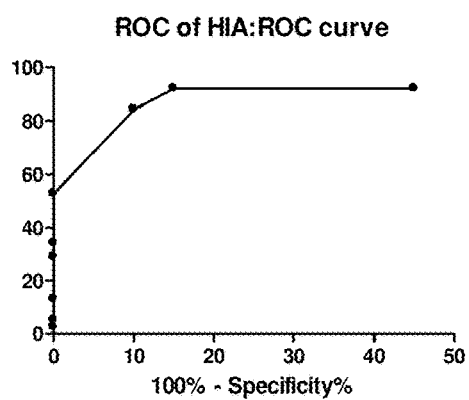
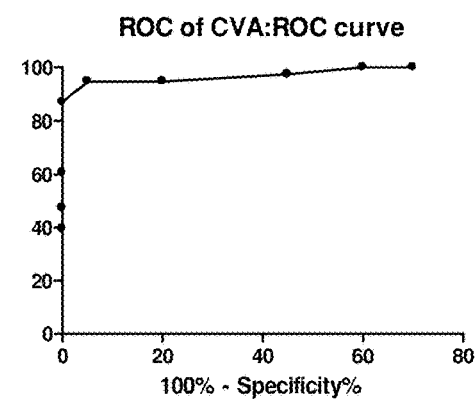
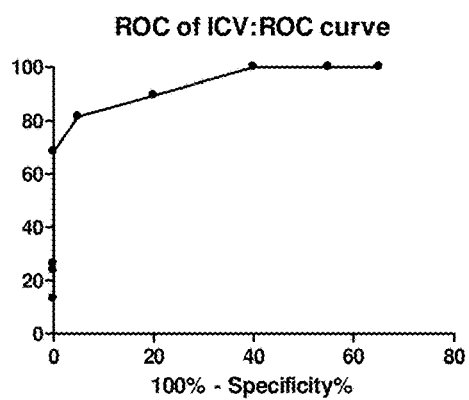

BIOMARKERS FOR GASTRIC CANCER AND USES THEREOF

PRIORITY CLAIM

This is a continuation of co-pending U.S. patent application Ser. No. 14/373,332, filed Jul. 18, 2014, which is the § 371 U.S. National Stage of International Application No. PCT/AU2013/000030, filed Jan. 17, 2013, which in turn claims the benefit of Australian Provisional Patent Application No. 2012900233, filed Jan. 20, 2012, both of which are herein incorporated by reference.

FIELD OF THE INVENTION

The present invention relates to the identification of biological markers associated with gastric cancer. Specifically, an association between gastric cancer and the differential expression of a number of proteins has been identified. The biological markers can be utilised for a range of purposes including methods for the diagnosis of gastric cancer, methods for identifying individuals susceptible to gastric cancer, and methods for assessing progression of gastric cancer.

BACKGROUND OF THE INVENTION

Gastric cancer (herein also referred to as "GC") is the fourth most common cancer in the world and the second leading cause of cancer mortality. In Western countries the expected 5-year survival rate at diagnosis is only 10-30%. This can be attributed to a paucity of diagnostic symptoms and subsequent endoscopic diagnosis at advanced stage. Unfortunately, when symptoms of GC present themselves metastasis has already occurred in >80% of cases.

Japan has one of the world's highest rates of GC. The implementation of a mass screening program of asymptomatic individuals by gastric photofluorography in Japan has increased the number of GC cases detected at the early-stage, improving the overall 5-year survival rate to more than 50%. The sensitivity and specificity of gastric photofluorography are good at 70-90% and 80-90%, respectively. However, cost-effectiveness studies have indicated that a gastric photofluorography program is not viable in Western countries where the incidence of GC is lower. A more suitable diagnostic approach would involve an accurate, non-invasive and cost-effective test for the detection of GC biomarkers involved in GC aetiology.

The existing clinical markers used in GC, carcinoembryonic antigen (CEA), carbohydrate antigen (CA) 19-9 and CA 72-4, are neither sufficiently sensitive nor specific for routine screening and are primarily used to monitor the progression of disease following treatment. The serum ratio of pepsinogen I/II has shown some promise as an alternative GC indicator in Asian populations, however, questions remain regarding its applicability in other racial groups including Western populations.

There are several profound obstacles associated with biomarker discovery for GC. Obtaining human samples of early-stage disease is difficult given its asymptomatic nature. The problem is further compounded by the genetic diversity of human populations and the influence of uncontrollable environmental factors meaning that potential biomarkers can be overshadowed by the high degree of natural variation in biomarker expression.

These aforementioned difficulties have led to a paucity of sensitive and specific biomarkers indicative of GC. Accordingly, the identification of new biomarkers suitable for detecting early-stage GC in a large population is urgently required.

Reference to any prior art in this specification is not, and should not be taken as, an acknowledgment or any form of suggestion that this prior art forms part of the common general knowledge in any country.

SUMMARY OF THE INVENTION

In addressing the aforementioned difficulties, the inventors have utilised a genetically engineered mouse model ($gp130^{F/F}$) of inflammation-associated GC. The $gp130^{F/F}$ mice spontaneously and reproducibly develop adenomas in the glandular part of the stomach that show all the progressive histological hallmarks associated with intestinal-type GC in humans arising from chronic infection with *H. pylori*. This has led to the identification of new biomarker indicators of early-stage GC.

Accordingly, in a first aspect, the present invention provides a method of diagnosing gastric cancer (GC) in a subject, the method including:

(a) measuring an expression level of one or more biomarkers in the subject, wherein the one or more biomarkers are selected from the group consisting of vitamin D binding protein (VDBP), clusterin, insulin like growth factor binding protein complex acid labile subunit (IGFALS), and afamin;

(b) comparing the expression level of the or each biomarker in the subject to a reference expression level for the or each biomarker; and (c) diagnosing GC in the subject on the basis of the comparison.

In one embodiment, the expression level of the one or more biomarkers is measured in a sample obtained from the subject. In one embodiment, the sample is a serum sample. In this regard, measuring the expression level of the one or more biomarkers includes measuring the level of biomarker protein in the sample. In one embodiment, the sample is a tissue sample. In this regard, measuring the expression level of the one or more biomarkers includes measuring the level of biomarker mRNA in the sample.

In some embodiments, the biomarker is human VDBP. In one embodiment, an expression level of VDBP in the subject that is lower than the reference expression level for VDBP is indicative of GC in the subject.

In some embodiments, the biomarker is human clusterin. In one embodiment, an expression level of clusterin in the subject that is lower than the reference expression level for clusterin is indicative of GC in the subject.

In some embodiments, the biomarker is human IGFALS. In one embodiment, an expression level of IGFALS in the subject that is higher than the reference expression level for IGFALS is indicative of GC in the subject.

In some embodiments, the biomarker is human afamin. In one embodiment, a level of afamin protein in the subject that is lower than the reference expression level for the afamin protein is indicative of GC in the subject.

In a second aspect, the present invention provides a method of determining if a subject is susceptible to developing gastric cancer (GC), the method including:

(a) measuring an expression level of one or more biomarkers in the subject, wherein the one or more biomarkers are selected from the group consisting of vitamin D binding protein (VDBP), clusterin, insulin like growth factor binding protein complex acid labile subunit (IGFALS), and afamin;

(b) comparing the expression level of the or each biomarker in the subject to a reference expression level for the or each biomarker; and (c) determining if the subject is susceptible to developing GC on the basis of the comparison.

In one embodiment, the expression level of the one or more biomarkers is measured in a sample obtained from the subject. In one embodiment, the sample is a serum sample. In this regard, measuring the expression level of the one or more biomarkers includes measuring the level of biomarker protein in the sample. In one embodiment, the sample is a tissue sample. In this regard, measuring the expression level of the one or more biomarkers includes measuring the level of biomarker mRNA in the sample.

In some embodiments of the second aspect of the invention, the biomarker is human VDBP. In one embodiment, an expression level of VDBP in the subject that is lower than the reference expression level for VDBP is indicative of GC in the subject.

In some embodiments of the second aspect of the invention, the biomarker is human clusterin. In one embodiment, an expression level of clusterin in the subject that is lower than the reference expression level for clusterin is indicative of GC in the subject.

In some embodiments of the second aspect of the invention, the biomarker is human IGFALS. In one embodiment, an expression level of IGFALS in the subject that is higher than the reference expression level for IGFALS is indicative of GC in the subject.

In some embodiments of the second aspect of the invention, the biomarker is human afamin. In one embodiment, a level of afamin protein in the subject that is lower than the reference expression level for the afamin protein is indicative of GC in the subject.

In a third aspect, the present invention provides a method of assessing progression of gastric cancer (GC) in a subject, the method including:

(a) measuring an expression level of one or more biomarkers in the subject, wherein the one or more biomarkers are selected from the group consisting of vitamin D binding protein (VDBP), clusterin, insulin like growth factor binding protein complex acid labile subunit (IGFALS), and afamin;

(b) comparing the expression level of the or each biomarker in the subject to a reference expression level for the or each biomarker; and (c) assessing the progression of GC in the subject on the basis of the comparison.

In one embodiment, the subject is undergoing treatment for the GC.

In some embodiments of the third aspect of the invention, the expression level of the one or more biomarkers is measured in a sample obtained from the subject. In one embodiment, the sample is a serum sample. In this regard, measuring the expression level of the one or more biomarkers includes measuring the level of biomarker protein in the sample. In one embodiment, the sample is a tissue sample. In this regard, measuring the expression level of the one or more biomarkers includes measuring the level of biomarker mRNA in the sample.

In some embodiments of the third aspect of the invention, the biomarker is human VDBP. In one embodiment, an expression level of VDBP in the subject that is lower than the reference expression level for VDBP is indicative of GC in the subject.

In some embodiments of the third aspect of the invention, the biomarker is human clusterin. In one embodiment, an expression level of clusterin in the subject that is lower than the reference expression level for clusterin is indicative of GC in the subject.

In some embodiments of the third aspect of the invention, the biomarker is human IGFALS. In one embodiment, an expression level of IGFALS in the subject that is higher than the reference expression level for IGFALS is indicative of GC in the subject.

In some embodiments of the third aspect of the invention, the biomarker is human afamin. In one embodiment, a level of afamin protein in the subject that is lower than the reference expression level for the afamin protein is indicative of GC in the subject.

In a fourth aspect, the present invention provides a method for screening a candidate therapeutic agent useful for treating gastric cancer (GC) in a subject, the method including assaying the candidate therapeutic agent for activity in modulating the expression level of one or more biomarkers selected from the group consisting of vitamin D binding protein (VDBP), clusterin, insulin like growth factor binding protein complex acid labile subunit (IGFALS), and afamin.

In one embodiment of the fourth aspect of the invention, the method includes the steps of:

(a) administering the candidate therapeutic agent to the subject;

(b) measuring the expression level of the or each biomarker in the subject; and (c) comparing the expression level of the or each biomarker in the subject to a reference expression level for the or each biomarker, wherein if the expression level of the or each biomarker approximates or is identical to the reference expression level for the or each biomarker, the candidate therapeutic agent is useful for treating GC in the subject.

In one embodiment of the fourth aspect of the invention, the method includes the steps of:

(a) exposing the candidate therapeutic agent to a cell expressing the or each biomarker;

(b) measuring for a change in the expression level of the or each biomarker in the cell; and (c) comparing the expression level of the or each biomarker in the subject to a reference expression level for the or each biomarker, wherein if the expression level of the or each biomarker approximates or is identical to the reference expression level for the or each biomarker, the candidate therapeutic agent is useful for treating GC in a subject.

In some embodiments of the fourth aspect of the invention, the candidate therapeutic agent increases the expression level of VDBP in the subject or cell to a level which approximates or is identical to the reference expression level for VDBP. In some embodiments, the candidate therapeutic agent increases the expression level of clusterin in the subject or cell to a level which approximates or is identical to the reference expression level for clusterin. In some embodiments, the candidate therapeutic agent decreases the expression level of IGFALS in the subject or cell to a level which approximates or is identical to the reference expression level for IGFALS. In some embodiments, the candidate therapeutic agent increases the expression level of afamin in the subject or cell to a level which approximates or is identical to the reference expression level for afamin.

In some embodiments of the aforementioned aspects of the invention, the method further includes measuring an expression level of the biomarker apolipoprotein E (ApoE) and/or the biomarker haptoglobin in the subject or cell.

In a fifth aspect, the present invention provides a kit for diagnosing gastric cancer (GC) in a subject, determining if a subject is susceptible to developing GC, or assessing progression of GC in a subject, the kit including means for measuring an expression level of one or more biomarkers in the subject, wherein the one or more biomarkers are selected from the group consisting of vitamin D binding protein (VDBP), clusterin, insulin like growth factor binding protein complex acid labile subunit (IGFALS), and afamin.

BRIEF DESCRIPTION OF THE FIGURES

For a further understanding of the aspects and advantages of the present invention, reference should be made to the following detailed description and Examples, taken in conjunction with the accompanying Figures.

FIGS. 2A-2E—(FIG. 2A) Schematic of the strategy used in Example 1 for the discovery, verification and validation of candidate serum protein biomarkers of gastric cancer (GC). Steps outlined with rectangular boxes were experimental processes while those represented by diamonds were analytical processes. The dashed line indicates that three proteins identified at Stage 1 bypassed verification at Stage 2 and underwent direct validation by ELISA in human samples at Stage 3. (FIG. 2B) Representative 2D gel spot map of a wild-type sample with non-GC phenotype. (FIG. 2C) Representative 2D gel spot map of a $gp130^{F/F}$ genotype mouse (FF) sample with GC phenotype. (FIG. 2D) Hierarchical clustering dendogram generated from the 512 matched spots. (FIG. 2E) Principal component analysis (PCA) scores plot generated from the 512 matched spots. The percentage of variance attributed to each principal component is shown.

FIG. 3—A flow-chart depicting the experimental workflow of used in Example 1 for the identification of candidate GC biomarkers based on the 38 multiple affinity removal system (MARS) depleted mouse serum samples. A sophisticated strategy involving multiple comparisons of the mouse genotypes, receiver operating characteristics (ROC) analysis, and candidate prioritization following mass spectrometry (MS) identification was then employed to select the eight most relevant proteins for verification and validation in human sera.

FIGS. 5A-5B—(FIG. 5A) A representative overlayed 2D DIGE image of a GC and non-GC sample showing the positions of the 38 spots-of-interest corresponding to eight candidate biomarker proteins identified in Example 1. Those spots identified as FINC MOUSE, ALS MOUSE, HPT MOUSE, and APOE MOUSE were up-regulated in GC and those identified as AFM MOUSE, SPA3K MOUSE, CLUS MOUSE, and VTDB MOUSE were down-regulated. (FIG. 5B) Box-and-whisker plots of matched spot volumes associated with the eight proteins of interest on the 2D DIGE. For all 38 spots, the mean spot volumes obtained for the GC phenotype group (i.e. FF/FFIL6 genotypes) were significantly different to the mean of the non-GC phenotype group (i.e. WT/IL6/FFStat3 genotypes) with Student's T-test P values <0.01.

(FIG. 6B) Western blot densitometry of mouse apoE, fibronectin, afamin, and clusterin. P values were calculated using a Mann-Whitney U test. Error bars represent the standard error of the mean. (FIG. 6C) Western blot detection of five candidate biomarkers in GC patient (n=11) and control (n=13) serum. The immunoglobulin light chain was used as an input control for densitometric analysis. (FIG. 6D) Western blot densitometry of human afamin, apoE, clusterin, fibronectin and haptoglobin. P values were calculated using a Mann-Whitney U test. Error bars represent the standard error of the mean.

(FIG. 7B) ROC curves obtained for the four proteins that demonstrated statistically significant differences in protein concentration between the GC patients and controls, and CA 72-4. Area Under the Curve (AUC) values for each are indicated.

FIG. 11—ROC curves obtained for secondary combinations of the five proteins (Afamin—A; Clusterin—C; Haptoglobin—H; IGFALS—I; VDBP—V) analysed in Example 2.

FIG. 12—ROC curves obtained for tertiary combinations of the five proteins (Afamin—A; Clusterin—C; Haptoglobin—H; IGFALS—I; VDBP—V) analysed in Example 2.

DETAILED DESCRIPTION OF THE INVENTION

Figure 1:
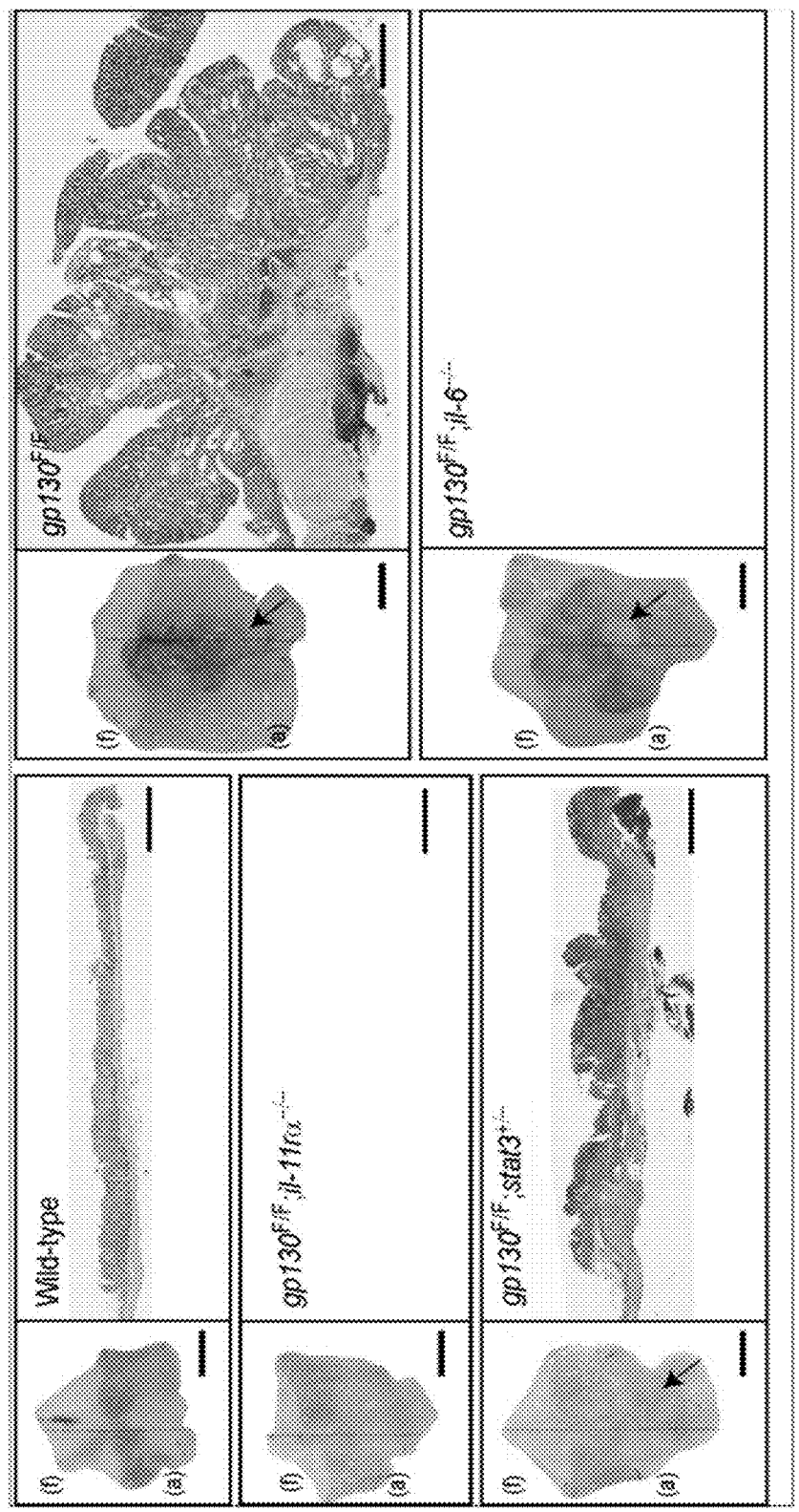
FIG. 1—Histological analysis pertaining to Example 1 was performed on week old mice of the indicated genotypes. Following excision of the stomach and opening along the outer curvature, stomachs were pinned out with the lumen facing the observer (insets). Longitudinal section along the dotted line were stained with H&E and oriented that the antrum faces to the left. Stomachs of all $gp130^{F/F}$ and $gp130^{F/F}$; $Il6^{-/-}$ mice reveal 4-6 distinct adenomatous tumours (arrow) within the glandular part of the antrum (a) that are characterized by elongated and often branching glands in association with inflammatory infiltrates (asterisk). Small regions of hyperplastic epithelium can be seen in $gp130^{F/F}$; $Stat3^{+/-}$ mice (arrowhead) suggestive of delayed and attenuated tumour formation[11]. The squamous epithelium of the fundus (f) never shows sign of hyperplasia. Bars are 200 µm (insets) and 50 µm (H+E sections).

The present invention is predicated in part on the identification of a number of biomarkers, the expression levels of which are altered in samples obtained from subjects with gastric cancer (GC). The differential expression of these biomarkers indicates that they are suitable markers which can form the basis of diagnostic and prognostic testing for GC.

A biomarker is effectively an organic biomolecule which is differentially present in a sample taken from a subject of one phenotypic status (e.g. having a disease) as compared with another phenotypic status (e.g. not having the disease). A biomarker is differentially present between different phenotypic status groups if the mean or median expression level of the biomarker is calculated to be different (i.e. higher or lower) between the groups. Therefore, biomarkers, alone or in combination, provide an indication that a subject belongs to one phenotypic status or another.

Accordingly, in a first aspect, the present invention provides a method of diagnosing gastric cancer (GC) in a subject, the method including:

(a) measuring an expression level of one or more biomarkers in the subject, wherein the one or more biomarkers are selected from the group consisting of vitamin D binding protein (VDBP), clusterin, insulin like growth factor binding protein complex acid labile subunit (IGFALS), and afamin;

(b) comparing the expression level of the or each biomarker in the subject to a reference expression level for the or each biomarker; and (c) diagnosing GC in the subject on the basis of the comparison.

Through the use of a genetically engineered mouse model ($gp130^{F/F}$) of inflammation-associated GC, the present inventors have determined that the aforementioned biomarkers are differentially expressed at an early stage in the development of gastric adenoma.

Accordingly, in a second aspect, the present invention provides a method of determining if a subject is susceptible to developing gastric cancer (GC), the method including:

(a) measuring an expression level of one or more biomarkers in the subject, wherein the one or more biomarkers are selected from the group consisting of vitamin D binding protein (VDBP), clusterin, insulin like growth factor binding protein complex acid labile subunit (IGFALS), and afamin;

(b) comparing the expression level of the or each biomarker in the subject to a reference expression level for the or each biomarker; and (c) determining if the subject is susceptible to developing GC on the basis of the comparison.

The term "gastric cancer" or "GC" as used thought the specification is taken to mean cancer of the stomach, including adenocarcinoma of the stomach. As would be understood by a person skilled in the art, the stomach includes the following four sections: cardia (including the cardial notch); fundus; body or corpus (including the angular incisure or notch); and pylorus (including the pyloric sphincter, pyloric antrum and pyloric canal). The term "gastric cancer" or "GC" also encompasses cancer of other regions of the gastrointestinal tract.

The methods of the aspects of the invention referred to above require measuring an expression level of one or more of the biomarkers VDBP, clusterin, IGFALS and afamin. These markers are discussed in detail below.

As used herein, the term "measuring an expression level" of a biomarker includes: (1) measuring the level of transcription of the corresponding gene into a messenger RNA (mRNA) molecule; and/or (2) measuring the level of translation of the mRNA into protein (i.e. measuring the level of protein per se); and/or (3) measuring the level of activity of the translated protein. In effect, the expression level of a biomarker can be measured at the RNA and/or protein stages of expression.

Accordingly, the term "biomarker" as used herein includes, but is not limited to, proteins (polypeptides), polynucleotides (e.g. mRNA) and/or metabolites whose expression level (e.g. level of transcription, level of translation, and/or level of activity) in a subject with gastric cancer, or in a sample taken from a subject with gastric cancer, is increased or decreased when compared to the expression level of the same biomarker in a normal sample (i.e. a reference expression level). Any biomarkers referred to herein also include their gene and protein synonyms as could be readily identified by a person skilled in the art.

The term "gene" is to be understood to mean a region of genomic nucleotide sequence (nuclear or mitochondrial) which includes a coding region that is transcribed and translated into protein. A "gene" in the context of the present invention can therefore include regulatory regions (e.g. promoter regions), transcribed regions, exons, introns, untranslated regions and other functional and/or non-functional sequence regions associated with the gene. Accordingly, in one embodiment the "expression level" of a biomarker in the subject or sample may be a reflection of the extent of transcription of the corresponding gene into mRNA in the subject or sample.

As would be understood by a person skilled in the art, a protein is a functional biomolecule composed primarily of amino acids, with the amino acid sequence determined by a corresponding gene. Accordingly, in one embodiment the "expression level" of a biomarker in the subject or sample may be a reflection of the extent of translation of mRNA of the corresponding gene into protein in the subject or sample.

Methods for measuring the level of translation of mRNA into protein are known in the art. For example, the level of a protein may be measured by techniques which include, but are not limited to, antibody-based testing (including Western blotting, immunoblotting, enzyme-linked immunosorbant assay (ELISA), radioimmunoassay (RIA), immunoprecipitation and dissociation-enhanced lanthanide fluoro immuno assay (DELFIA)), proteomics techniques, surface plasmon resonance (SPR), versatile fibre-based SPR, chemiluminescence, fluorescent polarization, phosphorescence, immunohistochemistry, immunofluorescence, matrix-assisted laser desorption/ionization mass spectrometry (MALDI-MS), as described in WO 2009/004576 (including surface enhanced laser desorption/ionization mass spectrometry (SELDI-MS), especially surface-enhanced affinity capture (SEAC), protein microarrays, surface-enhanced need desorption (SEND) or surface-enhanced photo label attachment and release (SEPAR)), matrix-assisted laser desorption/ionization time-of-flight (MALDI-TOF) mass spectrometry, microcytometry, microarray, microscopy, fluorescence activated cell sorting (FACS), and flow cytometry.

With respect to antibody-based testing methods such as immunohistochemistry and immunoblotting, antibodies or antisera, preferably polyclonal antisera, and most preferably monoclonal antibodies specific for each protein under investigation, are used to detect the protein abundance. The antibodies can be detected by direct labelling of the antibodies themselves, for example with radioactive labels, fluorescent labels, hapten labels such as, biotin, or an enzyme such as horseradish peroxidase or alkaline phosphatase. Alternatively, unlabelled primary antibody may be used in conjunction with a labelled secondary antibody, comprising antisera, polyclonal antisera or a monoclonal antibody specific for the primary antibody. Immunohistochemistry protocols and kits are well known in the art and are commercially available. Antibodies can be produced by methods well known in the art, for example, by immunizing animals with the protein under investigation.

Also contemplated are traditional immunoassays including, for example, sandwich immunoassays including ELISA or fluorescence-based immunoassays, as well as other enzyme immunoassays. Nephelometry is an assay performed in liquid phase, in which antibodies are in solution. Binding of the protein under investigation to the antibody results in a change in absorbance, which is measured. In the SELDI-based immunoassay, a biospecific capture reagent for the protein of interest is attached to the surface of an MS probe, such as a pre-activated ProteinChip array (see below). The protein is then specifically captured on the biochip through this reagent, and the captured protein is detected by mass spectrometry (see below).

A further technique for assessing protein levels using an antibody-based platform involves the versatile fibre-based surface plasmon resonance (VeSPR) biosensor, as described in PCT International Publication Number WO 2011/113085. Traditional SPR is a well-established method for label-free bio-sensing that relies on the excitation of free electrons at the interface between a dielectric substrate and a thin metal coating. The condition under which the incoming light couples into the plasmonic wave depends on the incidence angle and the wavelength of the incoming light as well as the physical properties (dielectric constant/refractive index) of the sensor itself and the surrounding environment. For this reason, SPR is sensitive to even small variations in the density (refractive index) in the close vicinity of the sensor, and does not require the use of fluorescent labels. The small variation of refractive index induced by the binding biomolecules such as proteins onto the sensor surface, can be measured by monitoring the coupling conditions via either the incidence angle or the wavelength of the incoming light. Existing SPR systems use the bulky and expensive Krestchmann prism configuration where one side of the prism is coated with a metal such as gold or silver that can support a plasmonic wave. Alternative SPR architectures have been developed based on optical fibres with the metallic coating deposited around a short section of the fibre. This approach reduces the complexity and cost of such sensors, opening a pathway to distinctive applications such as dip sensing. The material at the sensor surface is probed by monitoring the wavelength within a broad spectrum that is absorbed due to coupling to the surface plasmon. These techniques suffer from practical limitations associated with the need for careful temperature calibration, causing difficulty in analysing large numbers of samples consistently. A novel and powerful variant of an optical-fibre based SPR sensor, known as VeSPR, has been developed recently. VeSPR has a number of demonstrated advantages over existing SPR techniques including: (i) higher signal-to-noise ratio thus higher sensitivity; (ii) self-referencing of the transducing signal thus avoiding expensive/bulky temperature control; and (iii) the ability to perform multiplexed detection of different analytes using a single fibre.

Proteomics can also be used to analyse the expression level of a protein of interest present in a sample at a certain point of time. In particular, proteomic techniques can be used to assess the global changes of protein expression in a sample (also referred to as expression proteomics). Proteomic analysis typically includes: (i) separation of individual proteins in a sample by 2-D gel electrophoresis (2-D PAGE); (ii) identification of the individual polypeptides recovered from the gel, for example by mass spectrometry or N-terminal sequencing; and (iii) analysis of the data using bioinformatics.

Protein microarrays (also termed biochips) may also be used to determine the level of expression of a protein of interest in a sample. Many protein biochips are described in the art, including for example protein biochips produced by Ciphergen Biosystems, Inc. (Fremont, Calif.), Zyomyx (Hayward, Calif.), Invitrogen (Carlsbad, Calif.), Biacore (Uppsala, Sweden) and Procognia (Berkshire, UK). Examples of such protein biochips are described in the following patents or published patent applications: U.S. Pat. Nos. 6,225,047, 6,537,749, 6,329,209, and 5,242,828, and PCT International Publication Numbers WO 00/56934 and WO 03/048768.

The expression level of a protein of interest can also be measured by mass spectrometry, a method that employs a mass spectrometer to detect gas phase ions. Examples of mass spectrometers are time-of-flight, magnetic sector, quadrupole filter, ion trap, ion cyclotron resonance, electrostatic sector analyzer and hybrids of these. The mass spectrometer may be a laser desorption/ionization mass spectrometer. In laser desorption/ionization mass spectrometry, the protein or proteins to be detected are placed on the surface of a mass spectrometry probe, a device adapted to engage a probe interface of the mass spectrometer and to present the protein or proteins to ionizing energy for ionization and introduction into a mass spectrometer. A laser desorption mass spectrometer employs laser energy, typically from an ultraviolet laser, but also from an infrared laser, to desorb analytes from a surface, to volatilize and ionize them and make them available to the ion optics of the mass spectrometer. The analysis of proteins by LDI can take the form of MALDI or of SELDI, as described below.

The SELDI method is described, for example, in U.S. Pat. Nos. 5,719,060 and 6,225,047, and relates to a method of desorption/ionization gas phase ion spectrometry (e.g. mass spectrometry) in which an analyte (in this instance one or more of the proteins to be detected) is captured on the surface of a SELDI mass spectrometry probe. SELDI also encompasses affinity capture mass spectrometry, surface-enhanced affinity capture (SEAC) and immuno-capture mass spectrometry (icMS) as described by Penno M A et al., 2012 (*Res. Vet. Sci.*, 93: 611-617. These platforms involve the use of probes that have a material on the probe surface that captures proteins through a non-covalent affinity interaction (adsorption) between the material and the protein. The material is variously called an "adsorbent," a "capture reagent," an "affinity reagent" or a "binding moiety." Such probes can be referred to as "affinity capture probes" and as having an "adsorbent surface." The capture reagent can be any material capable of binding a protein. The capture reagent is attached to the probe surface by physisorption or chemisorption. The probes, which may take the form of a functionalised biochip or magnetic bead, may have the capture reagent already attached to the surface, or the probes are pre-activated and include a reactive moiety that is capable of binding the capture reagent, e.g. through a reaction forming a covalent or coordinate covalent bond. Epoxide and acyl-imidizole are useful reactive moieties to covalently bind protein capture reagents such as antibodies or cellular receptors. Nitrilotriacetic acid and iminodiacetic acid are useful reactive moieties that function as chelating agents to bind metal ions that interact non-covalently with histidine containing proteins. Adsorbents are generally classified as chromatographic adsorbents and biospecific adsorbents.

A chromatographic adsorbent refers to an adsorbent material typically used in chromatography. Chromatographic adsorbents include, for example, ion exchange materials, metal chelators (e.g. nitrilotriacetic acid or iminodiacetic acid), immobilized metal chelates, hydrophobic interaction adsorbents, hydrophilic interaction adsorbents, dyes, simple biomolecules (e.g. nucleotides, amino acids, simple sugars and fatty acids) and mixed mode adsorbents (e.g. hydrophobic attraction/electrostatic repulsion adsorbents).

A biospecific adsorbent refers to an adsorbent comprising a biomolecule, e.g. a nucleic acid molecule (e.g. an aptamer), a polypeptide, a polysaccharide, a lipid, a steroid or a conjugate of these (e.g. a glycoprotein, a lipoprotein, a glycolipid, a nucleic acid (e.g. DNA-protein conjugate). In certain instances, the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target protein than chromatographic adsorbents.

In general, a probe with an adsorbent surface is contacted with a sample being tested for a period of time sufficient to allow the protein under investigation to bind to the adsorbent. After an incubation period, the substrate is washed to remove unbound material. Any suitable washing solutions can be used; preferably, aqueous solutions are employed. The extent to which molecules remain bound can be manipulated by adjusting the stringency of the wash. The elution characteristics of a wash solution can depend, for example, on pH, ionic strength, hydrophobicity, degree of chaotropism, detergent strength, and temperature. Unless the probe has both SEAC and SEND properties (as described herein), an energy absorbing molecule then is applied to the substrate with the bound biomarkers.

In a further approach, the protein under investigation can be captured with a solid-phase bound immuno-adsorbent that has antibodies that specifically bind to the protein. After washing the adsorbent to remove unbound material, the protein is eluted from the solid phase and is detected by applying it to a biochip that binds the protein.

Proteins under investigation which are bound to the substrates are detected in a gas phase ion spectrometer such as a time-of-flight mass spectrometer. The proteins are ionized by an ionization source such as a laser, the generated ions are collected by an ion optic assembly, and then a mass analyzer disperses and analyzes the passing ions. The detector then translates information of the detected ions into mass-to-charge ratios. Detection of a protein typically will involve detection of signal intensity. Thus, both the quantity and mass of the protein can be determined.

Another method of laser desorption mass spectrometry is called surface-enhanced neat desorption (SEND). SEND involves the use of probes comprising energy absorbing molecules that are chemically bound to the probe surface ("SEND probe"). The phrase "energy absorbing molecules" (EAM) denotes molecules that are capable of absorbing energy from a laser desorption/ionization source and, thereafter, contribute to desorption and ionization of analyte molecules in contact therewith. The EAM category includes molecules used in MALDI, frequently referred to as "matrix," and is exemplified by cinnamic acid derivatives, sinapinic acid (SPA), cyano-hydroxy-cinnamic acid (CHCA) and dihydroxybenzoic acid, ferulic acid, and hydroxyaceto-phenone derivatives. The energy absorbing molecule may be incorporated into a linear or cross-linked polymer, e.g. a polymethacrylate. For example, the composition can be a co-polymer of α-cyano-4-methacryloyloxy-cinnamic acid and acrylate. Alternatively, the composition may be a co-polymer of α-cyano-4-methacryloyloxycinnamic acid, acrylate and 3-(tri-ethoxy)silyl propyl methacrylate, or may be a co-polymer of α-cyano-4-methacryloyloxycinnamic acid and octadecylmethacrylate ("Cl 8 SEND"). SEND is further described in U.S. Pat. No. 6,124,137 and PCT International Publication Number WO 03/64594.

SEAC/SEND is a version of laser desorption mass spectrometry in which both a capture reagent and an energy absorbing molecule are attached to the sample presenting surface. SEAC/SEND probes therefore allow the capture of proteins under investigation through affinity capture and ionization/desorption without the need to apply external matrix. The Cl 8 SEND biochip is a version of SEAC/SEND, comprising a Cl 8 moiety which functions as a capture reagent, and a CHCA moiety which functions as an energy absorbing moiety.

Another version of LDI is called surface-enhanced photolabile attachment and Release (SEPAR). SEPAR involves the use of probes having moieties attached to the surface that can covalently bind a protein, and then release the protein through breaking a photolabile bond in the moiety after exposure to light, e.g. to laser light. SEPAR and other forms of SELDI are readily adapted to detecting a protein or protein profile, as required by the methods of the present invention.

MALDI is a traditional method of laser desorption/ionization. In one MALDI method, the sample to be tested is mixed with matrix and deposited directly on a MALDI chip. Depending on the sample being tested, the protein being tested is preferably first captured with biospecific (e.g. an antibody) or chromatographic materials coupled to a solid support such as a resin (e.g. in a spin column). Specific affinity materials that may bind the protein being detected are described above. After purification on the affinity material, the protein under investigation is eluted and then detected by MALDI.

Analysis of proteins by time-of-flight mass spectrometry generates a time-of-flight spectrum. The time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing using specialized software. Data processing typically includes TOF-to-M/Z transformation to generate a mass spectrum, baseline subtraction to eliminate instrument offsets and high frequency noise filtering to reduce high frequency noise.

Data generated by desorption and detection of proteins can be analyzed with the use of a programmable digital computer. The computer program analyzes the data to indicate the number of proteins detected, and optionally the strength of the signal and the determined molecular mass for each protein detected. Data analysis can include steps of determining signal strength of a protein and removing data deviating from a predetermined statistical distribution. For example, the observed peaks can be normalized, by calculating the height of each peak relative to some reference. The computer can transform the resulting data into various formats for display. The standard spectrum can be displayed, but in one useful format only the peak height and mass information are retained from the spectrum view, yielding a cleaner image and enabling proteins with nearly identical molecular weights to be more easily seen. In another useful format, two or more spectra are compared, conveniently highlighting proteins that have varying expression levels between samples. Using any of these formats, one can readily determine whether a particular protein is present in a sample and to what level.

Analysis generally involves the identification of peaks in the spectrum that represent signal from a protein. Peak selection can be done visually, but commercial software can be used to automate the detection of peaks. In general, this software functions by identifying signals having a signal-to-noise ratio above a selected threshold and labelling the mass of the peak at the centroid of the peak signal. In one useful application, many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster.

Software used to analyze the data can include code that applies an algorithm to the analysis of the signal to determine whether the signal represents a peak in a signal that corresponds to a protein under investigation. The software also can subject the data regarding observed protein peaks to a classification tree or ANN analysis, to determine whether a protein peak or combination of protein peaks is present that indicates the status of the particular clinical parameter under examination. Analysis of the data may be "keyed" to a variety of parameters that are obtained, either directly or indirectly, from the mass spectrometric analysis of the sample. These parameters include, but are not limited to, the presence or absence of one or more peaks, the shape of a peak or group of peaks, the height of one or more peaks, the log of the height of one or more peaks, and other arithmetic manipulations of peak height data.

With respect to measuring the activity of a protein, the type of assay used will be dictated by the function of the protein under investigation. For example, VDBP is the major plasma carrier of vitamin $D_3$ and its metabolites and ensures that vitamin D is transported to the liver, $25(OH)_2D_3$ to the kidney, and $1.25(OH)_2D_3$ to target cells and organs. VDBP also plays an important role in macrophage activation that is distinct from its vitamin D-binding ability. For example, VDBP has been shown to enhance the leukocyte chemotactic activity of activated complement peptides, which are the precursor of the macrophage-activator factor. Such activities can form the basis of assaying for activity of the VDBP protein. With respect to clusterin, this protein has been implicated in a variety of activities including programmed cell death, regulation of complement mediated cell lysis, membrane recycling, cell-cell adhesion and src induced transformation. Clusterin also acts as a complement inhibitor as a part of the attack complex of complement. In performing these activities, clusterin binds to numerous partners such as immunoglobulins, lipids, heparin, bacteria, complement components, paraoxonase, beta amyloid, leptin and others. Such activities and binding partners can form the basis of assaying for activity of the clusterin protein. With respect to IGFALS, this protein is known to bind insulin-like growth factors, increasing their half-life and their vascular localization. For example, IGFALS binds insulin-like growth factor binding protein-3 (IGFBP-3) and so assays could be utilised which measure the extent of binding between the two proteins. Furthermore, afamin is known to possess vitamin E binding activity, and so assays which measure the amount or level of binding between the two will be a reflection of the level of afamin protein in a particular sample. This level can be compared to the level of binding in a normal control sample.

Methods for measuring the level of transcription of a gene into mRNA are also known in the art. For example, levels of mRNA may be measured by techniques which include, but are not limited to, Northern blotting, RNA in situ hybridisation, reverse-transcriptase PCR (RT-PCR), real-time (quantitative) RT-PCR, microarrays, or "tag based" technologies such as SAGE (serial analysis of gene expression). Microarrays and SAGE may be used to simultaneously quantitate the expression of more than one gene. Primers or probes may be designed based on nucleotide sequences of the genes or transcripts thereof. Methodology similar to that disclosed in Paik et al., 2004 (*NEJM*, 351(27): 2817-2826), or Anderson et al., 2010 (*Journal of Molecular Diagnostics*, 12(5): 566-575) may be used to measure the expression of one or more genes of interest. Many methods are also disclosed in standard molecular biology text books such as Sambrook et al. (*Molecular Cloning—A Laboratory Manual*, $3^{rd}$ Ed., Cold Spring Harbor Laboratory Press, 2000).

With respect to RT-PCR, the first step is typically the isolation of total RNA from a sample obtained from the subject under investigation. A typical sample in this instance would be a tissue sample, such as a gastric tumour sample (and corresponding normal gastric tissue if possible), although other sample sources are contemplated as described below. If the source of RNA is from a tumour, RNA can also be extracted, for example, from frozen or archived paraffin-embedded and fixed (e.g. formalin-fixed) tissue samples previously obtained from the subject. Messenger RNA (mRNA) may be subsequently purified from the total RNA sample. The total RNA sample (or purified mRNA) is then reverse transcribed into cDNA using a suitable reverse transcriptase. The reverse transcription step is typically primed using oligo-dT primers, random hexamers, or primers specific for the relevant gene, depending on the RNA template. The cDNA derived from the reverse transcription reaction then serves as a template for a typical PCR reaction. In this regard, two oligonucleotide PCR primers specific for the relevant gene are used to generate a PCR product. A third oligonucleotide, or probe, designed to detect a nucleotide sequence located between the other two PCR primers is also used in the PCR reaction. The probe is non-extendible by the Taq DNA polymerase enzyme used in the PCR reaction, and is labelled with a reporter fluorescent dye and a quencher fluorescent dye. Any laser-induced emission from the reporter dye is quenched by the quenching dye when the two dyes are located close together, as they are on the probe. During the PCR amplification reaction, the Taq DNA polymerase enzyme cleaves the probe in a template-dependent manner. The resultant probe fragments disassociate in solution, and signal from the released reporter dye is freed from the quenching effect of the second fluorophore. One molecule of reporter dye is liberated for each new molecule synthesized, and detection of the unquenched reporter dye provides the basis for quantitative interpretation of the data.

In real-time RT-PCR the amount of product formed, and the timing at which the product is formed, in the PCR reaction correlates with the amount of starting template. RT-PCR product will accumulate quicker in a sample having an increased level of mRNA compared to a standard or "normal" sample. Real-time RT-PCR measures either the fluorescence of DNA intercalating dyes such as Sybr Green into the synthesized PCR product, or can measure PCR product accumulation through a dual-labelled fluorigenic probe (i.e., TaqMan probe). The progression of the RT-PCR reaction can be monitored using PCR machines such as the Applied Biosystems' Prism 7000 or the Roche LightCycler which measure product accumulation in real-time. Real-time RT-PCR is compatible both with quantitative competitive PCR and with quantitative comparative PCR. The former uses an internal competitor for each target sequence for normalization, while the latter uses a normalization gene contained within the sample, or a housekeeping gene for RT-PCR.

The production and application of microarrays for measuring the level of expression of a gene at the transcriptional level are well known in the art. In general, in a microarray, a nucleotide sequence (for example an oligonucleotide, a cDNA, or genomic DNA) representing a portion or all of one or more of the relevant genes occupies a known location on a substrate. Typically, the substrate includes a multitude of nucleotide sequences such that one or more of the relevant genes can be assayed simultaneously. A nucleic acid target sample (for example total RNA or mRNA) obtained from a subject of interest is then hybridized to the microarray and the amount of target nucleic acid hybridized to each probe on the array is quantified and compared to the hybridisation which occurs to a standard or "normal" sample. One exemplary quantifying method is to use confocal microscope and fluorescent labels. The Affymetrix GeneChip™ Array system (Affymetrix, Santa Clara, Calif.) and the Atlas™ Human cDNA Expression Array system are particularly suitable for quantifying the hybridization; however, it will be apparent to those of skill in the art that any similar systems or other effectively equivalent detection methods can also be used. Fluorescently labelled cDNA probes may also represent the nucleic acid target sample. Such probes can be generated through incorporation of fluorescent nucleotides during reverse transcription of total RNA or mRNA extracted from a sample of the subject to be tested. Labelled cDNA probes applied to the microarray will hybridize with specificity to the equivalent spot of DNA on the array. Quantitation of hybridization of each arrayed element allows for assessment of corresponding mRNA abundance in the sample compared to the abundance observed in a standard or "normal" sample. With dual colour fluorescence, separately labelled cDNA probes generated from two sources of RNA are hybridized pairwise to the array. The relative abundance of the transcripts from the two sources corresponding to each specified gene is thus determined simultaneously. The miniaturized scale of the hybridization using microarray analysis affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels.

In the subject, the expression level of one or more of the proteins may be measured directly, or in an alternative embodiment, the expression level of one or more of the proteins may be measured in a sample obtained from a subject. It is to be made clear that the sample obtained from the subject that is analysed by the methods of the present invention may have previously been obtained from the subject, and, for example, has been stored in an appropriate repository. In this instance, the sample would have been obtained from the subject in isolation of, and therefore separate to, the methods of the present invention.

The sample which is obtained from the subject may include, but is not limited to, a blood sample, or a sample derived from blood (for example a serum sample or a plasma sample or a fraction of a blood, serum or plasma sample, blood cells), saliva, buccal swab, gastric fluid, stool sample, bladder washing, semen, urine, and a gastrointestinal tissue sample (such as a stomach or esophageal tissue sample). In certain circumstances, the sample may be manipulated in any way after procurement, such as by treatment with reagents, solubilization, or enrichment for certain components, such as the relevant protein or polynucleotide under investigation.

In one embodiment, the sample is a serum sample obtained from the subject. Serum is derived from blood plasma which is the yellow liquid component of blood, in which the blood cells in whole blood would normally be suspended. It makes up about 55% of the total blood volume. It is mostly water (90% by volume) and contains dissolved proteins, glucose, clotting factors, mineral ions, hormones and carbon dioxide. Blood plasma is prepared by spinning a tube of fresh blood in a centrifuge until the blood cells fall to the bottom of the tube. The blood plasma is then poured or drawn off. Blood plasma, preferably supplemented with a clotting inhibitor, e.g. heparin or EDTA, has a density of approximately 1.025 kg/l. Blood serum is blood plasma without fibrinogen or the other clotting factors (i.e. whole blood minus both the cells and the clotting factors).

In one embodiment, the sample is a tissue sample obtained from the subject. For example, the tissue sample may be a biopsy taken from the tumour. The tissue sample may be fixed and stored indefinitely or until analysis is conducted. Tissue sections taken from the sample may be stained for histological analysis and for conducting the assays referred to above to determine the level of biomarker protein present in the sample. Alternatively, RNA may be extracted from a tissue sample obtained from the subject and the RNA subject to the assays referred to above to determine the level of biomarker mRNA present in the sample. In instances where the sample is a tissue sample, ideally a sample of adjacent normal gastric tissue would be obtained for the purposes of comparison.

Once the expression level of the one or more biomarkers has been measured in the subject, or in a sample obtained from the subject, the expression level is compared to a reference expression level for each biomarker. The reference expression level for a particular biomarker is a level of expression of the biomarker that is associated with a known gastric cancer (GC) status, i.e. a level of expression which is known to be found in a subject not suffering from GC (a "normal" subject in the context of the present invention). A reference expression level for each biomarker may be derived from at least one normal subject and is preferably derived from an average of normal subjects (e.g. n=2 to 100 or more), wherein the subject or subjects have no prior history of GC. A reference expression level for each biomarker can also be obtained from one or more normal samples from a subject suspected to have GC. For example, a reference expression level for each biomarker may be obtained from at least one normal sample and is preferably obtained from an average of normal samples (e.g. n=2 to 100 or more), wherein the subject is suspected of having GC.

In some embodiments, the expression level of the one or more biomarkers may be increased in the sample being tested as compared to the reference expression level derived from one or more normal samples. In some embodiments, the expression level of the one or more biomarkers may be decreased in the sample being tested when compared to the reference expression level derived from one or more normal samples. This is described in further detail below.

As set out above, the methods of the invention involve measuring an expression level of one or more biomarkers selected from the group consisting of vitamin D binding protein (VDBP), clusterin, insulin like growth factor binding protein complex acid labile subunit (IGFALS), and afamin. Details of these biomarkers with respect to their associated genes and encoded proteins may be accessed from the GenBank database at the National Center for Biotechnology Information (available on the World Wide Web at ncbi.nlm.nih.gov). For example, the Gene ID number for human VDBP is 2638, human clusterin is 1191, human IGFALS is 3483, and human afamin is 173. The contents of these GenBank records are incorporated herein by reference.

In embodiments of the invention which require measuring the level of expression of one or more of the aforementioned biomarkers at the translational stage, for example measuring the level of protein per se, details of the amino acid sequence encoded by each biomarker can also be accessed from the GenBank database. For example, the human VDBP gene encodes three protein variants as represented by GenBank Accession Numbers NP_000574.2 (variant 1), NP_001191235.1 (variant 2) and NP_001191236.1 (variant 3). The human clusterin gene encodes the protein represented by GenBank Accession Number NP_001822.3. The human IGFALS gene encodes two protein variants as represented by GenBank Accession Numbers NP_001139478.1 (variant 1) and NP_004961.1 (variant 2). Finally, the human afamin gene encodes the protein represented by GenBank Accession Number NP_001124.1. Alternatively, details of the amino acid sequence encoded by each biomarker can be accessed from the UniProt database (available on the World Wide Web at uniprot.org) wherein the UniProt ID for the human VDBP protein (including each variant) is P02774, human clusterin protein is P10909, human IGFALS is Q8TAY0 (variant 1 and 2) and P35858 (variant 2), and human afamin protein is P43652.

In embodiments of the invention which require measuring the level of expression of one or more of the aforementioned biomarkers at the transcription stage, for example measuring mRNA levels of the corresponding genes, details of the transcribed nucleotide sequence(s) can also be accessed from the GenBank database. For example, the human VDBP gene is transcribed into three variants as represented by GenBank Accession Numbers NM_000583.3 (variant 1), NM_001204306.1 (variant 2) and NM_001204307.1 (variant 3). The human clusterin gene is also transcribed into three variants as represented by GenBank Accession Numbers NM_001831.3 (variant 1), NR_038335.1 (variant 2) and NR_045494.1 (variant 3). However, only transcript variant 1 encodes the functional protein. The human IGFALS gene is also transcribed into three variants as represented by GenBank Accession Numbers NM_001146006.1 (variant 1), NM_004970.2 (variant 2) and NR_027389.1 (variant 3). However, the third variant does not encode a functional protein. Finally, the human afamin gene is transcribed into the nucleotide sequence as represented by GenBank Accession Number NM_001133.2.

With reference to the two paragraphs above, it is to be made clear that reference to VDBP, clusterin, IGFALS and afamin includes a reference to naturally-occurring variants of these biomarkers. In this regard, a "variant" of a biomarker may exhibit an amino acid or nucleic acid sequence that is at least 80% identical, at least 90% identical, at least 95% identical, at least 98% identical, at least 99% identical, or at least 99.9% identical to the native biomarker. In some embodiments, a variant of a native biomarker may retain native biological activity or a substantial equivalent thereof.

In some embodiments, a variant may have no substantial biological activity, such as those variants which are precursors for the biologically active biomarker. Examples of naturally occurring variants of VDBP, clusterin, IGFALS and afamin are described above.

As used herein, the term "subject" refers to any animal (e.g. a mammal), including, but not limited to humans, non-human primates, dogs, cats, horses, cattle, sheep, deer, pigs, rodents, and any other animal known to get GC. Therefore, whilst human amino acid and mRNA sequences have been referred to above, it should be appreciated that the methods of the present invention are not limited to humans. Details of the specific proteins and their associated amino acid and mRNA sequences for different species may be readily accessed from the GenBank and UniProt databases (e.g. the Gene ID for *Mus musculus* VDBP is 14473, for clusterin is 12759, for IGFALS is 16005, and for afamin is 280662) or sequences may be identified by BLAST searching. In some instances, primers, probes or antibodies that may be used to measure protein/gene expression in one species may also be used for unrelated species.

In some embodiments, the biomarker may be VDBP, including for example human VDBP. In some embodiments, measuring the expression level of VDBP includes measuring the level of VDBP protein or mRNA in the subject, for example by using a method as described in detail above.

The inventors have found that an expression level of VDBP in a subject which is lower than the reference expression level for VDBP is indicative of GC in the subject, or indicates that the subject is susceptible to developing GC. Reference herein to "lower" with respect to the expression level of a biomarker as referred to herein, including VDBP, whether at the translational (protein) or transcriptional (mRNA) stage, is intended to mean, for example, at least a 1%, 5%, 10%, 20%, 30%, 40%, 50%, 60%, 70%, 80%, 90%, 100%, 1.1-fold, 1.2-fold, 1.3-fold, 1.4-fold, 1.5-fold, 1.6-fold, 1.7-fold, 1.8-fold, 1.9-fold, 2-fold, 2.1-fold, 2.2-fold, 2.3-fold, 2.4-fold, 2.5-fold, 2.6-fold, 2.7-fold, 2.8-fold, 2.9-fold, 3-fold, 3.1-fold, 3.2-fold, 3.3-fold, 3.4-fold, 3.5-fold, 3.6-fold, 3.7-fold, 3.8-fold, 3.9-fold, 4-fold, 5-fold, 5.1-fold, 5.2-fold, 5.3-fold, 5.4-fold, 5.5-fold, 5.6-fold, 5.7-fold, 5.8-fold, 5.9-fold, 6.0-fold, 10-fold, 20-fold, 50-fold, or 100-fold decrease in the expression level of the biomarker compared to the reference expression level.

In some embodiments, the biomarker may be clusterin, including for example human clusterin. In some embodiments, measuring the expression level of clusterin includes measuring the level of clusterin protein or mRNA in the subject, for example by using a method as described in detail above.

The inventors have found that an expression level of clusterin that is lower than the reference expression level for clusterin is indicative of GC in the subject, or indicates that the subject is susceptible to developing GC.

In some embodiments, the biomarker may be IGFALS, including for example human IGFALS. In some embodiments, measuring the expression level of IGFALS includes measuring the level of IGFALS protein or mRNA in the subject, for example by using a method as described in detail above.

The inventors have found that an expression level of IGFALS in a subject which is higher than the reference expression level for IGFALS is indicative of GC in the subject, or indicates that the subject is susceptible to developing GC. Reference herein to "higher" with respect to the expression level of a biomarker referred to herein, including IGFALS, whether at the translational (protein) or transcriptional (mRNA) stage, is intended to mean, for example, at least a 1%, 5%, 10%, 20%, 30%, 40%, 50%, 60%, 70%, 80%, 90%, 100%, 1.1-fold, 1.2-fold, 1.3-fold, 1.4-fold, 1.5-fold, 1.6-fold, 1.7-fold, 1.8-fold, 1.9-fold, 2-fold, 2.1-fold, 2.2-fold, 2.3-fold, 2.4-fold, 2.5-fold, 2.6-fold, 2.7-fold, 2.8-fold, 2.9-fold, 3-fold, 3.1-fold, 3.2-fold, 3.3-fold, 3.4-fold, 3.5-fold, 3.6-fold, 3.7-fold, 3.8-fold, 3.9-fold, 4-fold, 5-fold, 10-fold, 20 fold, 50-fold, or 100-fold increase in the expression level of the biomarker compared to the reference expression level.

In some embodiments, the biomarker may be afamin, including for example human afamin. In some embodiments, measuring the expression level of afamin includes measuring the level of afamin protein or mRNA in the subject, for example by using a method as described in detail above.

The inventors have found that an expression level of afamin that is lower than the reference expression level for afamin is indicative of GC in the subject, or indicates that the subject is susceptible to developing GC.

The identification of differential expression of the aforementioned biomarkers in GC also enables methods for assessing the therapeutic efficacy in a subject of a treatment for the GC.

Accordingly, in a third aspect, the present invention provides a method of assessing progression of gastric cancer (GC) in a subject, the method including:

(a) measuring an expression level of one or more biomarkers in the subject, wherein the one or more biomarkers are selected from the group consisting of vitamin D binding protein (VDBP), clusterin, insulin like growth factor binding protein complex acid labile subunit (IGFALS), and afamin;

(b) comparing the expression level of the or each biomarker in the subject to a reference expression level for the or each biomarker; and (c) assessing the progression of GC in the subject on the basis of the comparison.

In some embodiments of the present invention, an expression level of the one or more biomarkers is measured at more than one time points. Such "serial" sampling is well suited, for example, to monitoring the progression of gastric cancer. Serial sampling can be performed for any desired timeline, such as monthly, quarterly (i.e. every three months), semi-annually, annually, biennially, or less frequently. The comparison between the measured expression level in the subject and the reference expression level may be carried out each time a new sample is measured, or the data relating to levels may be held for less frequent analysis.

In one embodiment of the third aspect of the invention, the subject is undergoing treatment for the GC. The treatment may be a conventional therapy such as chemotherapy or radiotherapy, or the treatment may be an alternative therapy. In an alternative embodiment, the subject may not be undergoing treatment at all.

In some embodiments of the third aspect of the invention, measuring the expression level of the VDBP, clusterin, IGFALS, and/or afamin biomarkers includes measuring the level of VDBP, clusterin, IGFALS, and/or afamin protein or mRNA in the subject, or in a sample taken from the subject. In some embodiments, an expression level of VDBP, clusterin, and/or afamin that is lower than a reference expression level for each biomarker is indicative of progression of GC in the subject. In some embodiments, an expression level of IGFALS which is higher than a reference expression level for IGFALS is indicative of progression of GC in the subject.

In some embodiments, the method according to the third aspect of the invention may be used to perform clinical trials of a new drug, as well as to monitor the progress of a subject on the drug. Therapy or clinical trials involve administering the drug being tested in a particular regimen. The regimen may involve a single dose of the drug or multiple doses of the drug over time. The doctor or clinical researcher monitors the effect of the drug on the subject over the course of administration. If the drug has a pharmacological impact on the GC, the expression level of the aforementioned biomarkers will approximate or be identical to the reference expression level for the proteins. Therefore, the trending of the expression levels of the biomarkers can be monitored in the subject during the course of treatment. The expression level of the one or more biomarkers can be determined using the methods described in detail above. One embodiment of this method involves determining the expression levels of the aforementioned biomarkers for at least two different time points during a course of drug therapy, e.g. a first time and a second time, and comparing the change in expression levels of the biomarkers, if any. For example, expression level of the biomarkers can be measured before and after drug administration or at two different time points during drug administration. The effect of therapy is determined based on these comparisons. If a treatment is effective, the expression level of the aforementioned biomarkers will approximate or be identical to the reference expression level for the biomarkers, while if treatment is ineffective, the expression level of the aforementioned biomarkers will remain higher or lower than the reference expression level for the biomarkers.

In a fourth aspect, the present invention provides a method for screening a candidate therapeutic agent useful for treating gastric cancer, the method including assaying the candidate therapeutic agent for activity in modulating the expression level of one or more biomarkers selected from the group consisting of vitamin D binding protein (VDBP), clusterin, insulin like growth factor binding protein complex acid labile subunit (IGFALS), and afamin.

Screening assays may be performed in vitro and/or in vivo. For example, prospective agents may be screened to identify candidate therapeutic agents for the treatment of gastric cancer in a cell-based assay. In this regard, each prospective agent is incubated with cultured cells (for example cells obtained from the GI tract of a normal subject or from a subject suffering from gastric cancer, or cell lines derived from a normal or affected subject), and modulation of the expression level of a biomarker is measured. Accordingly, in one embodiment of the fourth aspect of the invention, the method includes:

(a) exposing the candidate therapeutic agent to a cell expressing the or each biomarker;

(b) measuring for a change in the expression level of the or each biomarker in the cell; and (c) comparing the expression level of the or each biomarker in the subject to a reference expression level for the or each biomarker, wherein if the expression level of the or each biomarker approximates or is identical to the reference expression level for the or each biomarker, the candidate therapeutic agent is useful for treating GC in a subject.

In another example, candidate therapeutic agents may be screened in organ culture-based assays. In this regard, each prospective agent is incubated with either a whole organ or a portion of an organ (such as a portion of the GI tract of a normal of affected subject) derived from a non-human animal and modulation of the expression level of the target biomarker is measured.

Screening methods may also employ administering prospective therapeutic agents to a subject suffering from gastric cancer. Accordingly, in one embodiment of the fourth aspect of the invention, the method includes measuring an expression level of the or each biomarker in the subject, wherein the expression level is measured after administration of the candidate therapeutic agent to the subject. The expression level of the or each biomarker in the subject is then compared to a reference expression level for the or each biomarker. If the expression level of the or each biomarker in the subject approximates or is identical to the reference expression level for each biomarker, the candidate therapeutic agent can be said to be useful for the treatment of GC. The expression level of the one or more biomarkers may be measured by the methods described in detail above.

In some embodiments of the fourth aspect of the invention the candidate therapeutic agent will increase the expression level of VDBP, clusterin or afamin, or will decrease the expression level of IGFALS, in the subject or cell to a level which approximates or is identical to the reference expression level for each biomarker.

The methods of the aforementioned aspects of the invention require the expression level of one or more of the VDBP, clusterin, IGFALS or afamin biomarkers to be measured. However, it would be well understood by a person skilled in the art that the expression level of other biomarkers may be measured in addition or concurrently with VDBP, clusterin, IGFALS and/or afamin. For example, biomarkers which are known to be differentially expressed in GC can also be incorporated into the methods of the invention.

For example, the inventors have also shown that apolipoprotein E (ApoE) and haptoglobin are differentially expressed in GC samples. Specifically, the expression levels of ApoE and haptoglobin are higher in GC samples than their expression level in "normal" samples. Therefore, the methods of the present invention may encompass measuring the expression level of one or more of VDBP, clusterin, IGFALS or afamin in combination with measuring the expression level of one or both of ApoE and haptoglobin. The expression level of ApoE and haptoglobin can be measured using the methods described in detail above.

Details of the ApoE and haptoglobin biomarkers may be accessed from the GenBank database at the National Centre for Biotechnology Information (available on the World Wide Web at ncbi.nlm.nih.gov). For example, the Gene ID number for human ApoE is 348, and human Haptoglobin is 3240. The contents of these GenBank records are incorporated herein by reference.

In embodiments of the invention which require measuring the level of expression of the ApoE and haptoglobin biomarkers at the translation stage, for example measuring the level of protein per se, details of the amino acid sequence encoded by each gene can also be accessed from the GenBank database. For example, the human ApoE gene encodes the protein represented by GenBank Accession Number is NP_000032.1, and the human haptoglobin gene encodes two protein variants represented by GenBank Accession Numbers NP_005134.1 (variant 1) and NP_0011195741.1 (variant 2). Alternatively, details of the amino acid sequence encoded by each of these biomarkers can be accessed from the UniProt database (available on the World Wide Web at uniprot.org) wherein the UniProt ID for the human ApoE protein is P02649, and human haptoglobin protein is P00738.

In embodiments of the invention which require measuring the level of expression of the ApoE and haptoglobin biomarkers at the transcription stage, for example measuring mRNA levels of the corresponding genes, details of the transcribed nucleotide sequence(s) can also be accessed from the GenBank database. For example, the human ApoE gene is transcribed into the nucleotide sequence as represented by GenBank Accession Number NM_000041.2. The human haptoglobin gene is transcribed into two variants as represented by GenBank Accession Numbers NM_005143.3 (variant 1) and NM_001126102.1 (variant 2).

In a fifth aspect, the present invention provides a kit for diagnosing gastric cancer (GC) in a subject, determining if a subject is susceptible to developing GC, or assessing progression of GC in a subject. The kit includes means for measuring an expression level of one or more biomarkers in the subject, wherein the one or more biomarkers are selected from the group consisting of vitamin D binding protein (VDBP), clusterin, insulin like growth factor binding protein complex acid labile subunit (IGFALS), and afamin.

In one embodiment, the kit includes a solid support, such as a chip, sensor, a microtiter plate or a bead or resin having a capture reagent attached thereon, wherein the capture reagent binds protein corresponding to one or biomarkers of the invention. Therefore, for example, the kit can comprise mass spectrometry probes for SELDI, such as ProteinChip® arrays, or a versatile fibre-based SPR sensing device. In the case of biospecific capture reagents, the kit can comprise a solid support with a reactive surface, and a container comprising the biospecific capture reagent.

In one embodiment, the kit can also include a washing solution or instructions for making a washing solution, in which the combination of the capture reagent and the washing solution allows capture of one or more of the biomarker proteins on the solid support for subsequent detection by, for example, mass spectrometry. The kit may include more than one type of adsorbent, each present on a different solid support.

In some embodiments, such a kit can include instructions for suitable operational parameters in the form of a label or separate insert. For example, the instructions may inform a consumer about how to collect the sample, how to wash the probe or the particular biomarker protein or proteins to be detected.

In some embodiments, the kit can include one or more containers with samples that represent a reference expression level for each biomarker, and are therefore to be used as standards for calibration.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

Finally, reference is made to standard textbooks of molecular biology that contain methods for carrying out basic techniques encompassed by the present invention. See, for example, Sambrook and Russell, *Molecular Cloning: A Laboratory Manual* (3rd edition), Cold Spring Harbor Laboratory Press, 2001.

The invention is further illustrated in the following examples. The examples are for the purpose of describing particular embodiments only and are not intended to be limiting with respect to the above description.

Example 1

Identification of Biomarkers for Gastric Cancer

The inventors have utilised the gp130$^{F/F}$ genetically engineered mouse (GEM) model of inflammation-associated gastric cancer (GC) for biomarker discovery followed by validation in human samples. As indicated above, the gp130$^{F/F}$ mice spontaneously and reproducibly develop adenomas in the glandular part of the stomach that show all the progressive histological hallmarks associated with intestinal-type GC in humans arising from chronic infection with *H. pylori*. Since gp130$^{F/F}$ mice harbour a phenylalanine (F) substitution mutation of a regulatory tyrosine residue in the cytokine receptor gp130, they respond with excessive Stat3 signalling to the cognate gp130 receptor ligands, including interleukin 6 (IL-6) and interleukin 11 (IL-11). Accordingly, the onset and progression of gastric tumourigenesis in gp130$^{F/F}$ mice is suppressed by genetically restricting the expression of Stat3 in compound gp130$^{F/F}$; Stat3$^{+/-}$ (FFStat3) mice. Surprisingly, genetic ablation of IL6 selectively normalizes the pan-inflammatory phenotype characteristic for gp130$^{F/F}$ mice without affecting gastric tumourigenesis in the corresponding gp130$^{F/F}$; Il6$^{-/-}$ (FFIL6) mice. As such, the different gp130$^{F/F}$ compound mutants enable genetic dissection of inflammation-associated gastric tumourigenesis, and the systemic, inflammatory acute phase response that is elicited by IL6 coincides with a variety of pathologies.

Materials and Methods

GEM Model

All experiments involving animals were approved by the Ludwig Institute for Cancer Research ethics committee. Production of gp130$^{F/F}$ (FF), gp130$^{F/F}$; Il6$^{-/-}$ (FFIL6), gp130$^{F/F}$; Stat3$^{+/-}$ (FFStat3), Il6$^{-/-}$ (IL6), and gp130$^{F/F}$; Il11rα$^{-/-}$ (FFIL11Ra) GEM has been described previously (see Jenkins B J et al., 2005, *Nat. Med.* 11: 845-852; Tebbutt N C et al., 2002, *Nat. Med.* 8: 1089-1097; Judd L M et al., 2009, *J. Pathol.* 217: 552-562; Ernst M et al., 2008, *J. Clin. Invest.* 118:1727-38). Age-matched littermates lacking mutations were designated as wild type (WT). Blood was collected by submandibular bleeding of 12-14 weeks of age directly into Microvette 500 Serum Gel tubes (Sarstedt, Nümbrecht, Germany). Samples were left standing at room temperature for 30 minutes prior to centrifugation at 6,600×g for 5 minutes to obtain serum. Serum supernatants were aliquoted into ~100 µL volumes and immediately stored at −80° C. (primary aliquots). On one occasion the samples were thawed on ice, re-aliquoted into 20 µL volumes and re-frozen at −80° C. (secondary aliquots). For Western blotting applications the secondary aliquots were thawed on ice, diluted 1/70 in ultrapure water, aliquoted in 6.5 µL volumes containing ~7 µg of total serum protein and re-frozen at −80° C. (tertiary aliquots).

Human Study Population

All experiments involving humans were approved by ethics committees of the Peter MacCallum Cancer Research Institute and the University of Adelaide. Sera from eleven preoperative GC patients with intestinal type gastric adenocarcinoma (Lauren classification) were accessed through the Peter MacCallum Cancer Research Institute Tissue Bank, and were stored in 100 µL primary aliquots at −80° C. Control serum was collected from 13 healthy volunteers with no reported gastrointestinal disease using Vacutte Z Serum Sep Clot Activator tube (Greiner Bio-One, Frickenhausen, Germany). The serum was clotted at room temperature for 20-40 minutes prior to centrifugation at 1,800×g for 10 minutes. Serum supernatants were aliquoted in 400 µL volumes (primary aliquots) and stored at −80° C. As with the mouse sera, secondary and tertiary preparations of human sera were made for verification purposes by enzyme-linked immunosorbant assay (ELISA) and Western blotting. Demographic information of the 24 human subjects is provided in Table 1.

TABLE 1

| Demographic variable | Characteristics | Gastric cancer (n = 11) | Healthy control (n = 13) |
|---|---|---|---|
| Age, y | Mean ± SD | 66.3 ± 10.7 | 57.8 ± 7.3 |
|  | Range | 51-79 | 50-72 |
| Sex, n | Male | 8 | 10 |
|  | Female | 3 | 3 |

Depletion of High Abundance Serum Proteins and 2D DIGE

Albumin, transferrin and IgG were depleted from the mouse sera using the Multiple Affinity Removal System (MARS, Agilent Technologies, Santa Clara, Calif.) with minor modifications to the manufacturer's recommendations. Briefly, Due to the relatively large number of GEM mice utilized in this investigation (n=38), serum samples were divided into two groups designated Experiment 1 (3×WT, 4×IL6, 4×FFStat3, 4×FF and 4×FFIL6) and Experiment 2 (4×WT, 3×IL6, 4×FFStat3, 4×FF and 4×FFIL6). Multiple affinity removal chromatography (MARS) depletion and 2D DIGE were performed separately for Experiments 1 and 2.

Secondary aliquots of sera (20 µL) were diluted in MARS Buffer A (90 µL) and filtered using 0.22 µm centrifugal devices (Agilent Technologies). Chromatography was performed using a Hewlett Packard 1090 HPLC system with 100 µL of dilute serum injected onto the MARS-M3 column (4.6×100 mm) at 0.5 mL/min. The instrument method was as follows: 0-10 minutes, 100% Buffer A at 0.5 mL/min; 10.01-17 minutes, 100% Buffer B at 1 mL/min; 17.01-28 minutes, 100% Buffer A at 1 mL/min. The flow-through peaks (2 mL) were collected on ice and cold 100% acetone (8 mL) was immediately added. Fractions in acetone were maintained at −20° C. for up to five days before the protein was recovered by centrifugation (5,000×g for 10 minutes at 10° C.). Protein pellets were washed once with cold 80% acetone (10 mL), resolubilized with TUC4% buffer (7 M urea, 2 M thiourea, 30 mM Tris, 4% CHAPS; 500 µL) and stored at −20° C. for up to one week. To further desalt the samples, thus ensuring their compatibility with isoelectric focusing (IEF), the depleted serum samples were thawed and subjected to two rounds of buffer exchange in TUC4% using 10 kDa MWCO Vivaspin 500 centrifugal devices (GE Healthcare, Uppsala, Sweden). The final samples were made up to ~200 µL with TUC4% and conductivities were assessed using a Horiba Twin Cond conductivity meter (model B-173, Horiba, Kyoto, Japan) to confirm levels were below 300 µS. The protein concentrations of the samples were determined via an EZQ assay (Invitrogen, Carlsbad, Calif.) as per the manufacturer's recommendations.

Lyophilized 25 nmol DIGE Fluor minimal Cy2, Cy3 and Cy5 CyDyes (GE Healthcare) were resuspended in 125 µL anhydrous N,N-Dimethylformamide (Sigma-Aldrich, St. Louis, Mo.) to produce 200 pmol/µL stock solutions. The stocks were aliquoted (1 µL) into screw cap tubes and stored under argon at −80° C. for >12 months without appreciable loss of sensitivity. When required for labelling the appropriate volumes of the individual depleted sera samples containing 70 µg of protein were added directly to the Cy3 and Cy5 aliquots (dye/protein ratio of 200 pmol/70 µg). Dye swaps of biological replicates were performed to control for potential dye-associated bias. Separate internal standards were prepared for each of the two experiment (refer to Results section) by pooling 35 μg of protein from samples included in the particular experiment (with minor exceptions). The internal standard was labelled with Cy2 at a ratio of 200 pmol dye/70 μg protein. Labelling reactions were performed on ice for 30 minutes in darkness and quenched with the addition of 1 μL of 10 mM lysine per 200 pmol of dye. The appropriate Cy3 and Cy5 samples were combined with 70 μg of the internal standard and sufficient amounts of TUC4% to bring the samples to equivalent volumes (refer to Supplementary Tables 1 and 2). Dithiothreitol (DTT, Sigma-Aldrich) and pH 4-7 carrier ampholytes (IPG buffer; GE Healthcare) were also added such that the final samples contained 210 μg protein, 7 M urea, 2 M thiourea, 30 mM Tris, 4% w/v CHAPS, 10 mM DTT, 0.5% v/v ampholytes plus a trace amount of bromophenol blue for color. The sample volumes were reduced to ~150 μL using 10 kDa molecular weight cut-off Vivaspin 500 centrifugal devices (5-10 minutes at 8,200×g; GE Healthcare) prior to cup-loading onto 24 cm 4-7 Immobiline DryStrips (GE Healthcare), which had been rehydrated overnight in 450 μL of rehydration buffer (TUC4% containing 0.5% v/v ampholytes, 1.2% v/v DeStreak reagent [GE Healthcare] and trace bromophenol blue). Requisite Cy3, Cy5 and Cy2 samples were combined for electrophoretic separation. IEF in the first dimension was carried out using an IPGphor II (GE Healthcare) for 70,000 total Vhours.

Following IEF the strips were equilibrated for 15 minutes in reducing buffer (50 mM Tris-HCl pH 8.8, 6 M urea, 30% v/v glycerol, 2% w/v SDS, 1% w/v DTT) then alkylating buffer (as above with 2.5% w/v of iodoacetamide (IAA) in place of DTT). The strips were sealed on top of 2DGel DALT NF 12.5% pre-cast gels (Serva Electrophoresis, Heidelberg, Germany) using a molten solution of 1% w/v low melting point agarose in proprietary cathode buffer (Serva Electrophoresis). Fluorescently labelled ECL Plex Rainbow markers (GE Healthcare) were included on a selected few gels. Protein separation in the second dimension was carried out using an EttanDALT 12 unit (GE Healthcare) in the presence of the anode and cathode buffers (Serva Electrophoresis) at 25° C. using a three phase program: (1) 50 V; 5 mA/gel for 1 hour, (2) 100 V; 10 mA/gel for 1 hour, (3) 250 V; 30 mA/gel for 14 hours. Gels were scanned using an Ettan DIGE Imager (GE Healthcare) at 100 μm resolution using the following exposures: Cy2 channel, 0.4 seconds; Cy3 channel, 0.07 seconds; Cy5 channel 0.1 seconds. Once scanned the gels were stored without fixation at −80° C. until required for spot picking.

Comparative Image Analysis

Image analysis was undertaken using DeCyder 2D software (Versions 6.5 and 7.0, GE Healthcare). Each gel image was processed separately in the Differential In-gel Analysis (DIA) module of DeCyder prior to export to the Biological Variation Analysis (BVA). In DIA spot detection was performed based on an estimated 10,000 spots with an exclusion filter rejecting spots with volumes <30,000. Background subtraction and in-gel normalization were carried out automatically by the software. The DIA workspaces were imported into BVA for manual spot matching to the master gel. Manual spot matching was required due to the large number of spot trains that were not effectively matched when the task was performed by the software. The same user-defined master gel was used for Experiments 1 and 2 to ensure consistency of spot identities. In Experiment 1, the master gel also constituted an analytical gel. In Experiment 2, the master gel was exported into BVA for this purpose only and was not included in the statistical analyses.

Multivariate statistical testing by hierarchical clustering and principal component analysis (PCA) was performed using the Extended Data Analysis (EDA) module of DeCyder (Version 7.0) based on spots that were detected in >70% of the gels. For univariate statistical testing, normalized volumes of the matched spots were exported from DeCyder into Excel (Microsoft, Redmond, Wash.). Standardized abundance values (herein referred to as "spot volumes") were produced by dividing the spot volumes of the Cy3 and Cy5 channels by the Cy2 channel for each gel. The spot volumes were then $\log_{10}$ transformed to normally distribute the data and, for each group within a given comparison, the standard deviation (SD) of each spot was calculated. Unpaired two-tailed Student's T-tests were also performed in Excel based on the $\log_{10}$ transformed spot volumes and P values were cross-referenced with those obtained by DeCyder to confirm they were equivalent. The post-hoc power calculation for each comparison was performed using Piface (version 1.64, available on the World Wide Web at cs.uiowa.edu/~rlenth/Power/) (Lenth R V, 2007, *J. Anim. Sci.* 85: E24-29) as described previously (Penno M A et al., 2009, *J. Proteome Res.* 8: 2812-2826). Briefly, for each group under consideration the 75% percentile value of all standard deviations of matched spot volumes was used as the measure of σ (Karp N A and Lilley K S, 2005, *Proteomics*, 5: 3105-3115), the significance level was set at 0.01 (a), the required power was 80% and the number of biological replicates was specific to each group (n). The resulting effect sizes were exponentiated to reverse the $\log_{10}$ transformation, thereby providing the minimum fold-change at which the mean spot volume of the compared groups could be considered significantly different. To account for the problem of multiple hypotheses testing (Karp N A et al., 2007, *Mol. Cell Proteomics*, 6: 1354-1364), q-values were determined for each matched spot using an Excel spreadsheet developed by Dr Graham Horgan of Biomathematics and Statistics Scotland (downloaded from the World Wide Web at rowett.ac.uk/~gwh/qval.xls). The P values for a given comparison were exported into the spreadsheet and q-values were calculated based on the equations of Storey J D and Tibshirani R, 2003 (*Proc. Natl. Acad. Sci. USA*, 100: 9440-9445).

To qualify as being differentially expressed spots were required to fulfill four criteria:

1. Spots were required to be present on >70% of spot maps (i.e. ≥27/38). 512 spots fulfilled this criterion and were considered in subsequent analyses.
2. Spots were required to have an unpaired two-tailed Student's T-tests P value <0.01 based on $\log_{10}$ transformed spot volumes for a given comparison.
3. The determined fold-change in spot volume was required to be >a magnitude of 2.1 for Comparison 1, also 2.1 for Comparison 2 and 1.8 for Comparison 3 as determined by post-hoc power calculations. Fold-changes were calculated based on mean spot volumes and not the $\log_{10}$ transformed volumes. Expression values less than 1 (i.e. whereby a spot was down-regulated in one group versus the other in the comparison) were divided into −1 to reflect that change.
4. Spots were required to have a q-value <0.01 to control for the high false discovery rate associated with multiple hypothesis testing.

Further statistical testing by receiver operating characteristics (ROC) analysis of 2D DIGE data was performed in Excel.

Protein Identification

Spots of interest were excised from the analytical gels using an Ettan Spot Cutting Robot (GE Healthcare) based on pick lists generated in DeCyder. Plugs were pooled from 2-6 gels for overnight digestion with trypsin (100 ng of sequencing grade modified trypsin [Promega, Fitchburg, Wis.] in 20 µL of 5 mM ammonium bicarbonate, 10% acetonitrile [ACN]). The extracted tryptic peptides were separated using an 1100 HPLC system equipped with a Protein ID Chip column assembly (40 nL trap column with 0.075×43 mm C-18 analytical column) housed in an HPLC-Chip Cube (all Agilent Technologies). This was interfaced directly with an HCT Ultra 3D-Ion-Trap mass spectrometer (Bruker Daltonics, Billerica, Mass.) operating in positive ion mode. The column was equilibrated with 0.1% FA, 3% ACN at 0.5 µL/min and the samples eluted with an ACN gradient (3%-31% over 32 minutes). Ionizable species (300<m/z<1, 200) were trapped and one or two of the most intense ions eluting at the time were fragmented by collision-induced dissociation. Active exclusion was used to exclude a precursor ion for 30 seconds following the acquisition of two spectra. MS and MS/MS spectra were subjected to peak detection and de-convolution using DataAnalysis (Version 3.4, Bruker Daltonics). The MS and MS/MS mass lists were exported into BioTools (Version 3.1, Bruker Daltonics) then submitted to Mascot (Version 2.2). The searching specifications were: database=SwissProt 56.4, taxonomy=Mammalia (63826 sequences), enzyme=trypsin, fixed modifications=carbamidomethylation of cysteine, variable modifications=oxidation of methionine, peptide mass tolerance=±0.3 Da, fragment mass tolerance=±0.4 Da, missed cleavages=1, and peptide charge=1+, 2+ and 3+. Protein identifications were made on the basis of having at least two matching peptides with ion scores above the specified threshold. Matches to trypsin and contaminating human keratins were ignored. When redundancy in protein identification was observed, for example, when different protein isoforms were matched to a list of identical masses, only the most suitable database entry corresponding to the full length sequence and/or the entry to which additional masses were matched to isoform-specific regions of the protein were considered. When multiple proteins were identified within a spot only the entry with the largest emPAI score was considered in as the major constituent of the spot and thus the likely contributor to its differential regulation (Ishihama Y et al., 2005, *Mol. Cell. Proteomics*, 4: 1265-1272). Human homologues of mouse proteins were identified using the BLAST function of UniProt (available on the World Wide Web at uniprot.org/blast/) (UniProt Consortium, 2011, *Nucl. Acids Res.* 39: D214-219).

Western Blotting

Tertiary aliquots containing 6.5 µL of diluted serum were mixed with 2.5 µL of NuPAGE LDS Sample Buffer (4×) (Invitrogen) and 1 µL of 0.5M DTT. Samples were heated at 95° C. for 5 minutes and then 10 µL volumes were loaded per lane on a NuPAGE Novex 4-12% Bis-Tris Gel (Invitrogen). The ten mouse samples chosen for further validation were run on a single gel with results validated by two technical repeats with the exception of clusterin, which was analysed in a single experiment. The 24 human samples were run on three separate gels simultaneously, with each gel containing equal numbers of GC patient samples and age (where possible)/gender matched controls. Gels were run at 200 V for 50 minutes with NuPAGE MOPS SDS Running Buffer (Invitrogen) and transferred to Immobilon-P PVDF membranes (Millipore, Billerica, Mass.) at 15 V for 50 minutes with Towbin buffer (0.025 M TRIS, 0.192 M glycine, 20% methanol). After transfer, membranes were stained with AmidoBlack staining solution (0.1% (w/v) amido black [Naphthol blue black, Sigma-Aldrich] in 10% (v/v) acetic acid) and digitally scanned before destaining in methanol. Membranes were then blocked in 5% skim milk for 1 hour at room temperature, and incubated overnight at 4° C. with primary antibodies against target proteins. The six primary antibodies used in this investigation were:
1. Rabbit anti-human afamin (Abcam, Cambridge, England)
2. Rabbit anti-mouse apolipoprotein E (apoE) (Thermo, Rockford, Ill.)
3. Mouse anti-human apoE (Abcam)
4. Rabbit anti-human apolipoprotein J (clusterin) (Abcam)
5. Rabbit anti-human fibronectin (Abcam)
6. Rabbit anti-human haptoglobin (Sigma-Aldrich)

Following overnight incubation in the primary antibody, membranes were washed 3× with TBS-T (50 mM Tris, 150 mM NaCl, 0.05% Tween 20, pH 7.6), then incubated for 1 hour at room temperature with a horseradish peroxidase (HRP)-conjugated secondary antibody. The horseradish peroxidase (HRP)-conjugated secondary antibodies were: (1) rabbit anti-mouse IgG-HRP (Rockland, Gilbertsville, Pa.), (2) goat anti-rabbit IgG-HRP (Thermo), and (3) goat anti-mouse IgG-HRP (Thermo). Membranes were washed a further 3× with TBS-T then detected with Sigma Enhanced Chemiluminescent Peroxidase Substrate (Sigma-Aldrich or Millipore) and autographic film (Agfa, Mortsel, Belgium). Western Blot densitometry was performed using ImageJ (National Institutes of Health; available on the World Wide Web at rsb.info.nih.gov/ij/) or ImageQuant TL (Version 7.0, GE Healthcare). The intensities of the bands of interest were normalized to the intensity of the immunoglobulin light-chain band evident on the AmidoBlack stained membrane at ~25 kDa to control for potential differences in gel loading. For each protein, the distributions of normalized intensity values for GC and non-GC groups were exported to GraphPad Prism (Version 5; GraphPad Software, La Jolla, Calif.) and compared using a non-parametric Mann-Whitney test with a significance threshold of P<0.05.

Enzyme-Linked Immunosorbent Assays

Enzyme-linked immunosorbent assays (ELISAs) were performed in accordance with the manufacturer's recommendations. The nine ELISA kits used in this investigation were:
1. Afamin ELISA kit (Uscnk, Wuhan, P.R. China)
2. Human apolipoprotein E ELISA (Mabtech, Sweden)
3. Quantikine human clusterin ELISA kit (R&D Systems, Minneapolis, Minn.)
4. QuantiMatrix ELISA fibronectin kit (Millipore, Billerica, Mass.)
5. Haptoglobin human ELISA kit (Abcam)
6. Human alpha 1-anti-chymotrypsin ELISA (Kamiya, Seattle, Wash.)
7. Vitamin D binding protein ELISA (Kamiya)
8. Insulin like growth factor binding protein acid labile subunit ELISA kit (Uscn, China)
9. Carbohydrate antigen (CA) 72-4 ELISA, human (Kamiya)

Serum protein concentrations were interpolated from kit-specific standard curves generated in GraphPad Prism (GraphPad Software). Resulting serum protein concentrations were standardized against the mean concentration obtained for each measured protein in the control group. This facilitated the cross-candidate comparisons of the markers on an equivalent scale (Faca V M et al., 2008, *PLoS Med.* 5: e123). Mann-Whitney U tests (two-tailed, significance threshold P<0.05) and ROC were performed in GraphPad Prism.

Results
Biology of the FF Mutant Mice

Homozygous gp130$^{F/F}$ mutant mice spontaneously and reproducibly develop distinct adenomas in the glandular part of the stomach that become histologically visible as 3-5 individual lesions by approximately 4-6 weeks of age. They continuously grow over the following 2-3 months to yield a maximal tumour burden of approximately 250 mg, and thus contributing to 0.8-1% of the overall body weight of these mice. These tumours occur with 100% penetrance and irrespective of the genetic background of the mice. It has been shown previously that these lesions replicate many of the progressive histological hallmarks associated with intestinal-type GC in humans arising from chronic infection with *H. pylori* (Jenkins B J et al., 2005, *Nat. Med.* 11: 845-852; Tebbutt N C et al., 2002, *Nat. Med.* 8: 1089-1097; Ernst M, Jenkins B J. 2004, *Trends Genet.* 20:23-32. And Correa P et al. 1975, *Lancet* 2:58-60). Accordingly, these lesions simultaneously show hallmarks of atrophic gastritis, intestinal metaplasia and epithelial dysplasia, yet they rarely progress to adenocarcinomas. Since tumourigenesis is attenuated following anti-microbial treatment or genetic impairment of Toll-receptor mediated signalling, these gp130$^{F/F}$ GEM represent a preclinically validated model for early stage inflammation-associated intestinal-type GC in human.

Since gp130$^{F/F}$ GEM harbour a phenylalanine substitution mutation of a regulatory tyrosine residue in the cytokine receptor gp130, these mice respond with excessive Stat3 signalling to the cognate gp130 receptor ligands that include IL6 and IL11. Accordingly, the onset and progression of gastric tumourigenesis in FF mice is suppressed and delayed by genetically restricting the expression of the latent transcription factor Stat3 in compound FFStat3 mice (Jenkins B J et al., 2005, *Nat. Med.* 11: 845-852) (FIG. 1). Surprisingly, genetic ablation of IL6 selectively normalizes the pan-inflammatory phenotype characteristic for FF mice without affecting gastric tumourigenesis in the corresponding FFIL6 mice. Likewise, the overall survival of FFIL6 is improved compared to that of FF mice, suggesting that their pan-inflammatory response rather than their tumour burden becomes rate limiting for survival. By contrast, FFIL11Rα mice, which lack expression of the IL11-specific IL11Rα receptor subunit and therefore are unable to respond to IL11, fail to develop gastric tumours and survival of FFIL11Rα mice remained similar to that of their IL11Rα proficient counterparts. Since ablation of only one Il11rα allele in gp130$^{F/F}$; Il11rα$^{/+}$ delayed and attenuated tumourigenesis, pharmacological interference with IL11-dependent gp130/Stat3 activation reduced overall tumour burden in FF mice with established disease [Ernst 2008, and data not shown]. Thus, partitioning of the phenotypes between FFIL6 and FFIL11Rα mice enables genetic separation between the systemic, IL6-mediated inflammatory responses and the IL11-dependent promotion of gastric adenoma formation. Meanwhile, global genetic restriction of Stat3 expression in compound FFStat3 mice impaired IL11-dependent tumourigenesis as well as IL6-dependent systemic inflammation (Jenkins B J et al., 2005, *Nat. Med.* 11: 845-852).

Identification of Serum Biomarkers for GC in the GEM Model

The biomarker identification workflow employed in this investigation can be broadly categorised into three stages. The discovery stage examined sera collected from the genetic engineered mouse (GEM) model of gastric cancer (GC) to identify differentially expressed proteins as candidate serum biomarkers. The second stage applied the semi-quantitative technique of Western blotting to verify the differential expression of a subset of candidate biomarkers in the GEM model. The third stage tested biomarkers verified in the mouse against human sera of GC patients and healthy controls using Western blotting and also the clinically relevant diagnostic platform, the quantitative ELISA (FIG. 2A).

Figure 2B:
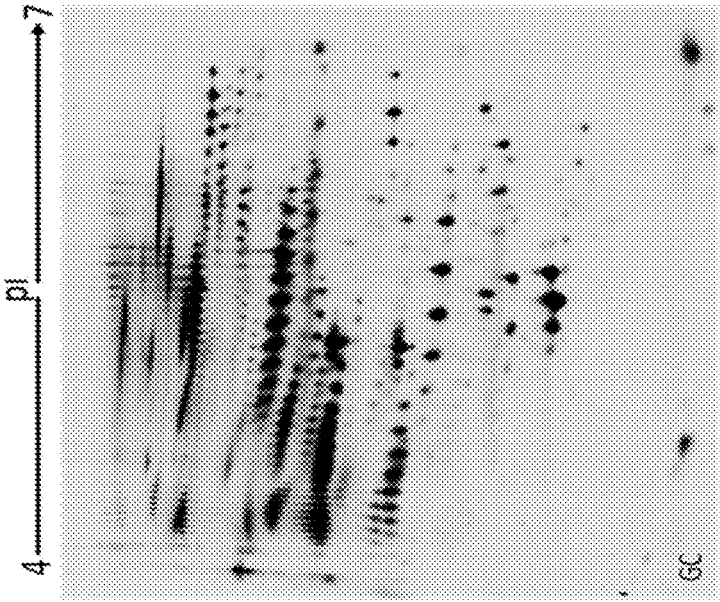
Figure 2C:
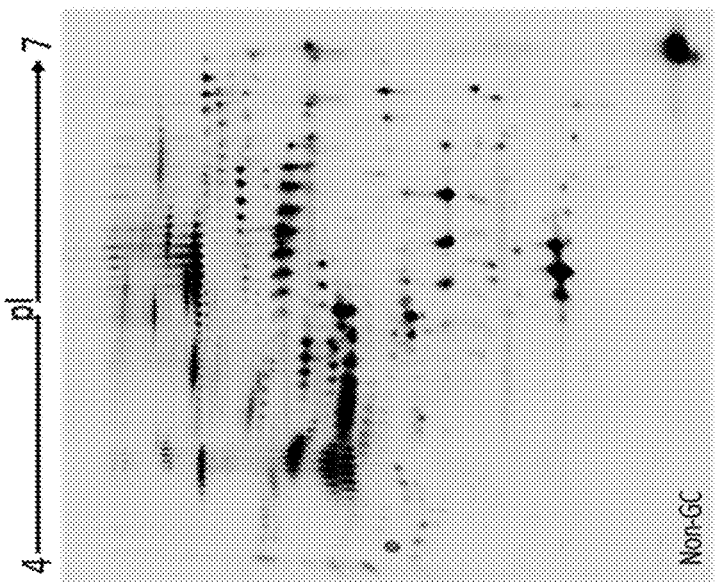
Figure 2E:
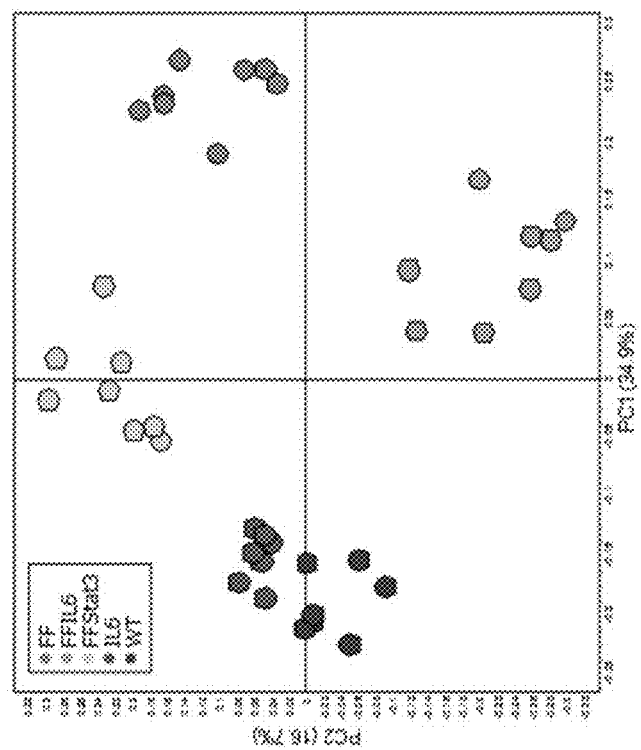
Figure 2D:
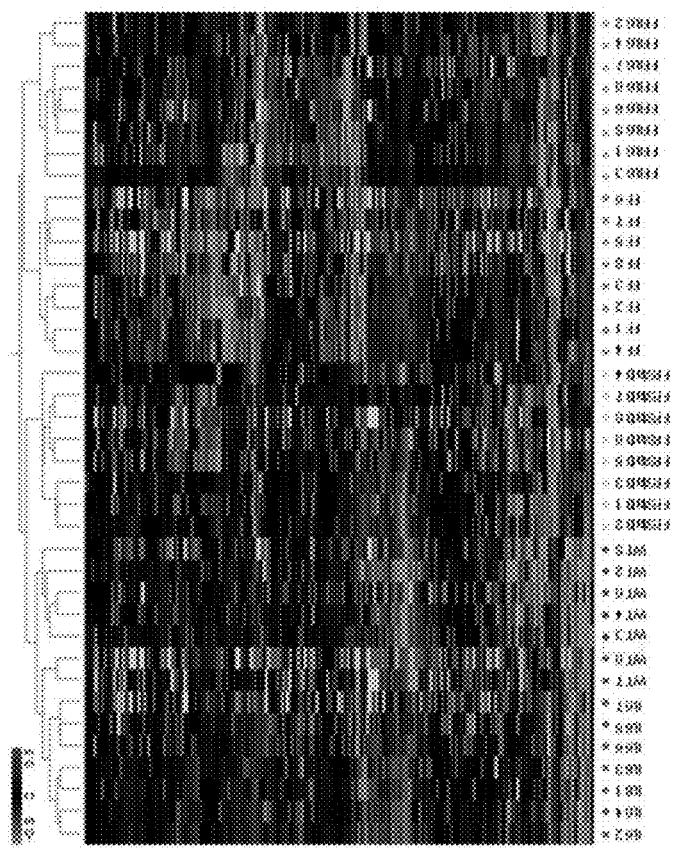

At the discovery phase, MARS depleted sera from 16 GC phenotype mice represented by the FF/FFIL6 genotypes, and 22 non-GC phenotype mice represented by the FFStat3/WT/IL6 genotypes, were analysis by 2D DIGE generating 38 spot maps. Representative spot maps of GC and non-GC phenotype sera are shown in FIG. 2B. Using the DeCyder software, a total of 512 spots were matched to >70% of spot maps (i.e. ≥27 of 38) and were included in subsequent statistical analyses. Unsupervised hierarchical clustering based on the 512 matched spot volumes revealed clusters based on mouse genotype at the lowest level of the hierarchy and on the GC versus non-GC phenotype at higher levels (FIG. 2C). Principal component analysis also revealed distinct groupings based on genotype with a clear dichotomy between the GC and non-GC mice (FIG. 2D), suggesting that the expression of several matched spots was linked to the GC phenotype. Furthermore, the predominant separation of the GC and non-GC groups based on the first principal component highlighted that the phenotype was the major source of variation within the experiment.

A filtering strategy was developed to distinguish between which of the 512 matched gel spots were regulated in association with the IL6-mediated acute phase response versus those that were associated with GC (i.e. the candidate biomarkers). This process is summarized graphically in FIG. 3. Initially, three comparisons of the volumes of the 512 matched spots were made facilitated by the inclusion of multiple mutant genotypes in the study. In the first comparison, the spots of the seven WT mice were compared to the seven IL6 mice using T-tests ($P<0.01$), calculations of the false discovery rate ($q<0.01$) and a post-hoc power calculation (fold change>magnitude 2.1; refer to Supplementary Information Section 1.4). In the second comparison, the 512 spot volumes of the eight FF mice were compared to the eight FFIL6 mice using the same parameters described for comparison 1. In the third comparison, the 16 GC phenotype mice (FF/FFIL6 genotypes) were compared to the 22 non-GC phenotype (WT/IL6/FFStat3 genotypes) mice also using T-tests ($P<0.01$), calculations of the false discovery rate ($q<0.01$) and a post-hoc power calculation with a minimum fold-change of magnitude 1.8. The results, summarized in a Venn diagram (shown in FIG. 3), indicated that three spots were differentially abundant in association with the IL6 knockout in the absence of GC ($C_1$), 51 spots were associated with the $IL_6$ knockout in the presence of GC ($C_2$), while 10 spots were associated with the IL6 knockout independently of GC ($C_1/C_2$ intersection). Seventeen spots were likely IL6-mediated acute phase response proteins regulated in GC ($C_2/C_3$ intersection), and 132 spots were differentially abundant in GC ($C_3$).

Figure 4:
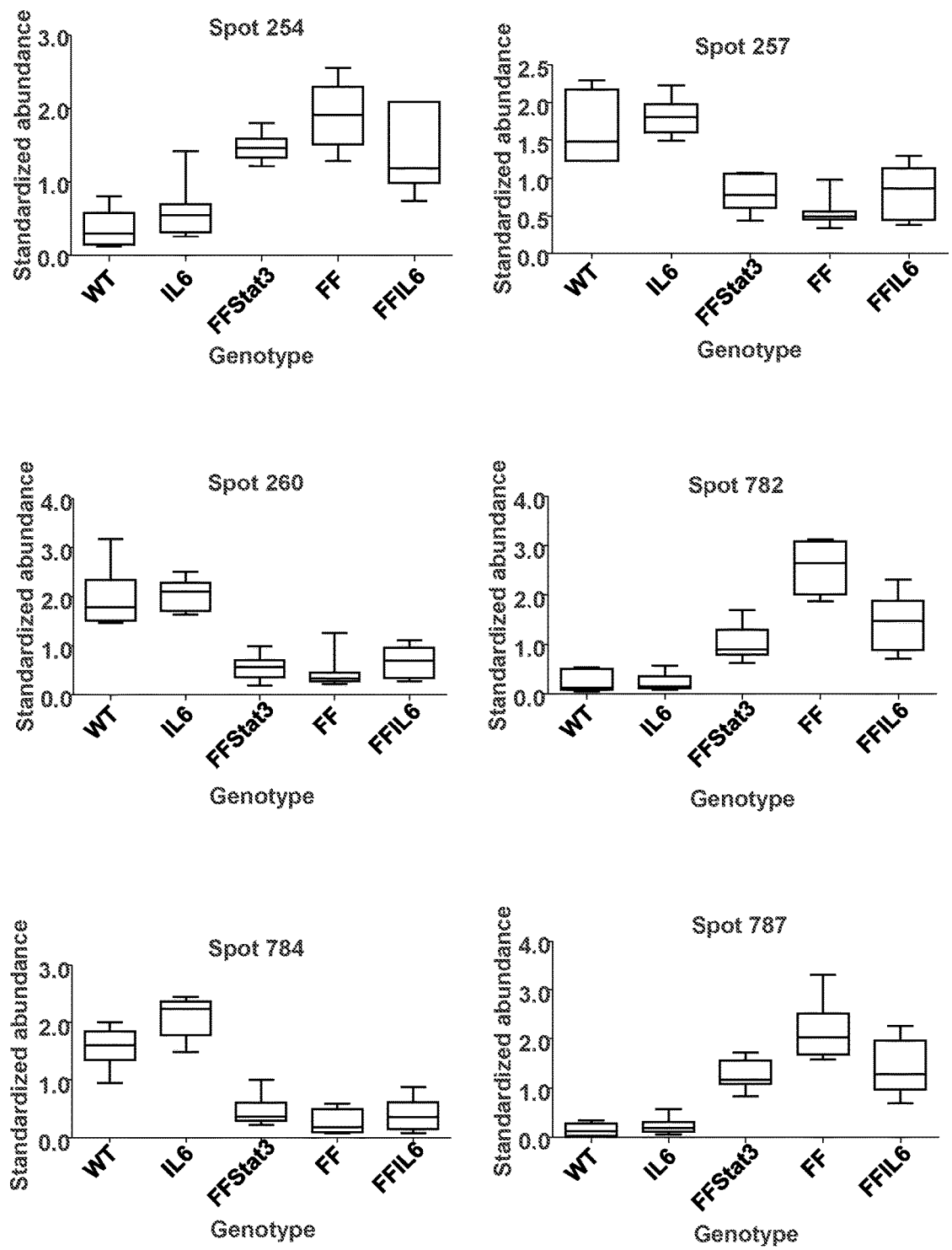
FIG. 4—Box-and-whisker plots of the standardized abundance values, also referred to as volumes, of two-dimensional difference in-gel electrophoresis (2D DIGE) spots identified in Example 1 and found to be associated with the $gp130^{F/F}$ mutation rather than the GC phenotype.
Figure 4:
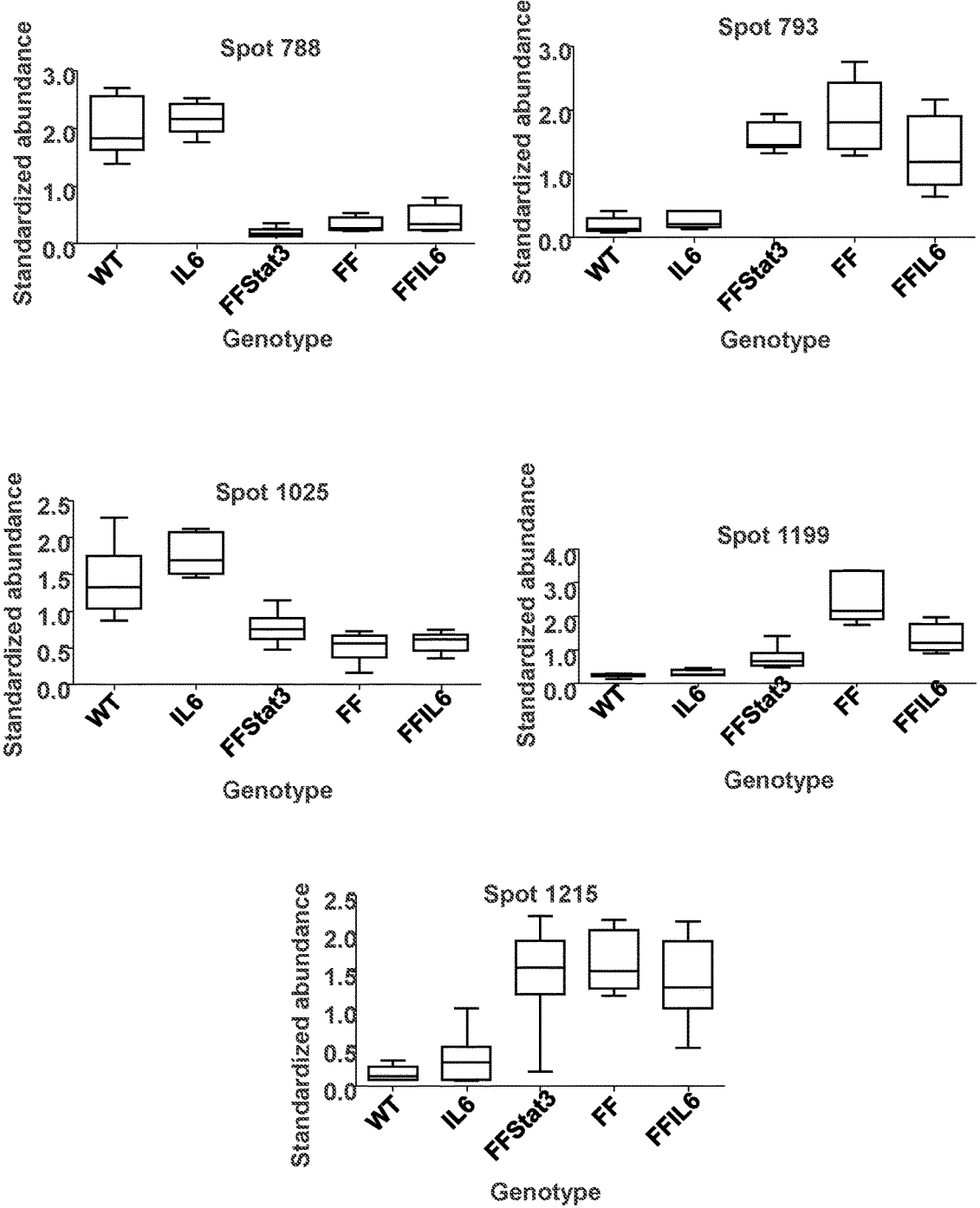

The capabilities of the 132 GC-associated spot volumes to distinguish between GC and non-GC phenotypes were further explored using ROC analysis. Two ROC calculations on the volumes of each spot were performed. In $ROC_1$, the GC phenotype (FF/FFIL6 genotypes) was considered positive and non-GC (WT/IL6/FFStat3 genotypes) negative. Nine spots returned area-under-the-curves ($AUC_1$) values <0.85 and were excluded from the dataset. In $ROC_2$, the FF mutation was considered positive (FF/FFIL6/FFStat3 genotypes) and wild-type gp130 was considered negative (WT/IL6 genotypes). Eleven spots returned $AUC_2 > AUC_1$ values signifying they were more similarly and significantly regulated in those mice carrying the FF mutant genotype than the GC versus non-GC phenotype. Visual inspection of the box-and-whisker plots associated with these spots confirmed their apparent association with the FF mutation (FIG. 4). In summary, of the initial 132 GC-associated spots, nine were considered insufficient discriminators of the GC versus non-GC phenotype and 11 appeared to be associated with the gp130 mutation. Interestingly, eight of the 11 FF mutation-associated spots were found to contain liver carboxylesterase N as the predominant protein component (UniProt identifier ESTN_MOUSE, SwissProt accession number P23953, data not shown). The significance of this protein in relation to the gp130 mutation is unclear. This resulted in 112 spots of interest that were specifically regulated and differentially abundant in GC versus non-GC phenotype mice independent of IL-6 signalling.

The 112 GC-associated spots were analyzed by liquid chromatography MS (as described above under "Protein identification"), leading to the identification of 31 different murine proteins corresponding to 28 human protein homologues. Given this relatively large number of proteins, a prioritization strategy was used to expedite the process of candidate verification and validation (Cima I et al., 2011, Proc. Natl. Acad. Sci. USA, 108: 3342-3347; and Surinova S et al., 2011, J. Proteome Res. 10: 5-16).

Firstly, only those proteins demonstrating global regulation (i.e. all identified spots containing these proteins were either up or down regulated—refer to Table 2) were considered, as the expression of such candidates could be more easily explored using well characterized technologies such as Western blotting and ELISAs.

Secondly, the online bioinformatics resource DAVID (the Database for Annotation, Visualization and Integrated Discovery; National Institute of Allergy and Infectious Diseases, National Institutes of Health; available on the World Wide Web at david.abcc.ncifcrf.gov/home.jsp) (Huang da W et al., 2009, Nat. Protoc. 4: 44-57; and Huang da W et al., 2009, Nucl. Acids Res. 37: 1-13) was used to explore and summarize the known associations between the candidates and biological pathways, tissue-specific patterns of expression, and disease classes.

Thirdly, previous associations of the candidates with GC in the literature were considered. Lastly, the magnitude of fold-change observed in the 2D DIGE experiment was also considered.

TABLE 2

| Protein Uniprot ID Accession number | Spot[a] | Spot fold-change[b] | Average fold-change[b] | Human homologue Uniprot ID Accession number | % seq. identity[c] | Pathologies associated with direction of expression[c] |
|---|---|---|---|---|---|---|
| Afamin AFAM_MOUSE O89020 | 628 631 634 637 667 668 689 | -1.9 -2.1 -2.5 -2.8 -1.8 -2.3 -3.2 | ↓ -2.4 | Afamin AFAM_HUMAN P43652 | 67% | Ovarian cancer, hepatocellular carcinoma |
| Apolipoprotein E APOE_MOUSE P08226 | 1330 1332 | 2.1 2.2 | ↑ 2.1 | Apolipoprotein E APOE_HUMAN P02649 | 71% | Gastric cancer, hepatocellular carcinoma, colorectal cancer, head and neck cancer, prostate cancer, breast cancer |
| Clusterin CLUS_MOUSE Q06890 | 1233 | -2.0 | ↓ -2.0 | Clusterin CLUS_HUMAN P10909 | 76% | Prostate tumors, degenerative scoliosis, rheumatoid arthritis |
| Fibronectin FINC_MOUSE P11276 | 121 123 126 127 196 116 117 122 | 2.4 2.6 2.4 2.1 3.3 2.1 2.2 2.7 | ↑ 2.5 | Fibronectin FINC_HUMAN P02751-7 | 90% | Chronic hepatitis, rheumatoid arthritis, various cancers, hyperthyroidism, preeclampsia, systemic lupus erythematosus, coronary artery disease, pregnancy, aging |
| Haptoglobin HPT_MOUSE Q61646 | 1191 1196 1204 1207 1208 1209 | 10.1 3.2 2.3 3.1 2.6 3.5 | ↑ 4.1 | Haptoglobin HPT_HUMAN P00738 | 80% | Gastric cancer, Acute phase response, rheumatoid arthritis, biliary obstruction, nephritis, ulcerative colitis, aplastic anemia, major depression, corticosteroid therapy, androgen use, XM model of GC |
| Insulin-like growth factor-binding protein complex acid labile chain ALS_MOUSE P70389 | 660 | 3.2 | ↑ 3.2 | Insulin-like growth factor-binding protein complex acid labile subunit ALS_HUMAN P35858 | 77% | Excessive growth hormone therapy, preeclampsia |
| Serine protease inhibitor A3K SPA3K_MOUSE P07759 | 119 120 150 412 423 425 430 437 438 | -3.6 -3.6 -3.7 -2.7 -4.3 -4.9 -5.4 -5.2 -3.6 | ↓ -4.1 | Alpha-1-antichymotrypsin AACT_HUMAN P01011 | 57% | Nephrotic syndrome, status asthmaticus, cold urticaria, newborns/infants |

TABLE 2-continued

| Protein Uniprot ID Accession number | Spot[a] | Spot fold-change[b] | Average fold-change[b] | Human homologue Uniprot ID Accession number | % seq. identity[c] | Pathologies associated with direction of expression[c] |
|---|---|---|---|---|---|---|
| | 966 | −3.7 | | | | |
| | 967 | −4.8 | | | | |
| Vitamin D-binding protein VTDB_MOUSE P21614 | 988 | −3.5 | ↓ | Vitamin D-binding protein VTDB_HUMAN P02774 | 77% | Type I diabetes, liver fibrosis |
| | 1018 | −2.6 | −3.1 | | | |

[a]Refers to the master spot number on the 2D DIGE gels assigned in DeCyder;
[b]Refers to the fold-change in spot volume between GC mice (FF/FFIL6 genotypes) and non-GC mice (WT/IL6/FFStat3 genotypes) observed in the 2D DIGE experiment;
[c]Refers to the sequence identity between the mouse protein and human homologue determined using BLAST.

Based on these four considerations, a subset of eight proteins representing 38 spots on the 2D gels were identified as candidate biomarkers of follow-up analyses, namely, afamin, alpha-1-antichymotrypsin (AACT, human homologue of murine serine protease inhibitor A3K), apolipoprotein E (apoE), clusterin, fibronectin, haptoglobin, insulin like growth factor binding protein complex acid labile subunit (IGFALS) and vitamin D binding protein (VDBP)(see Table 2). The MS summary statistics of the 38 spots is provided in Table 3.

Figure 5B:
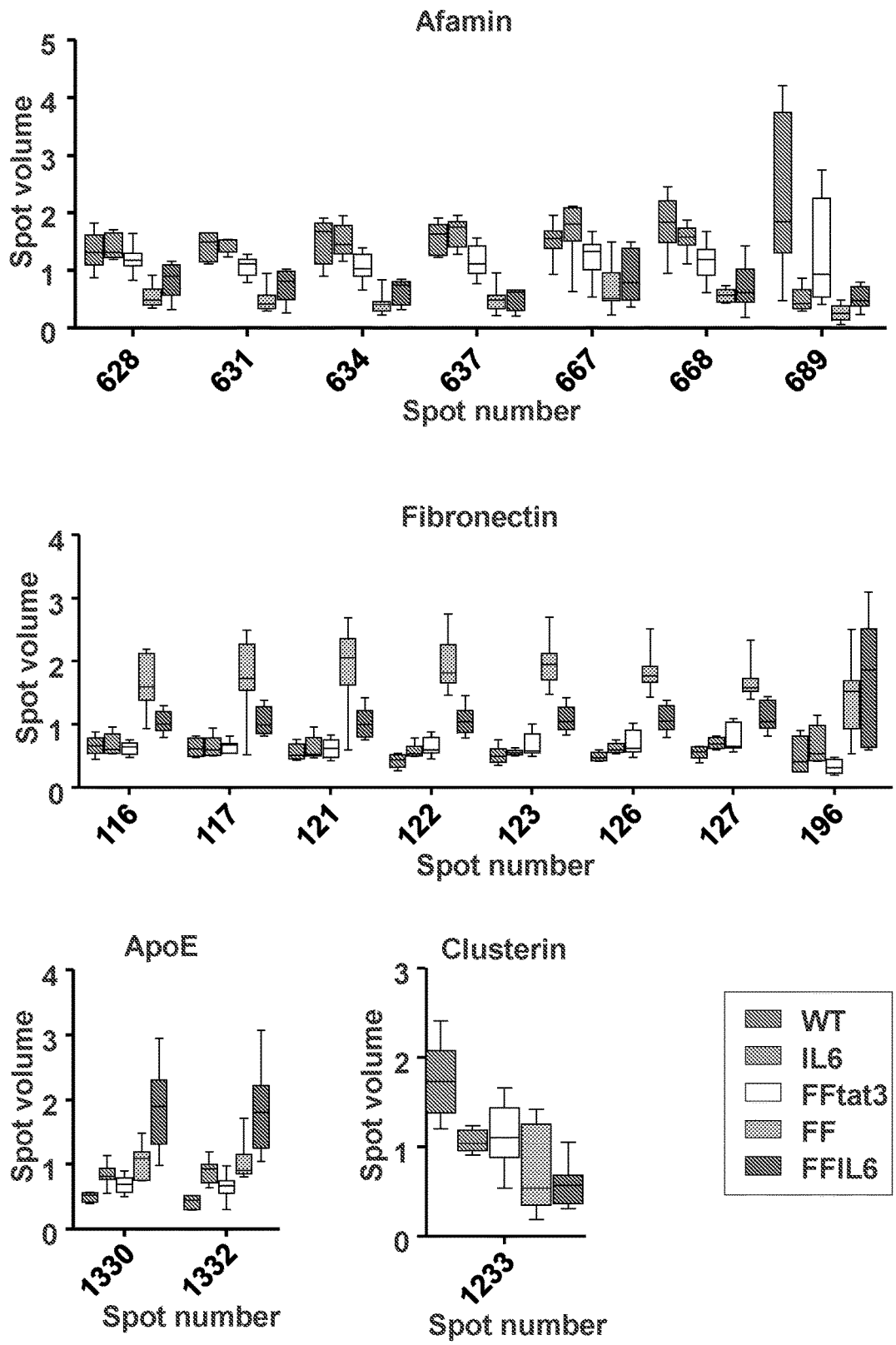
Figure 5B:
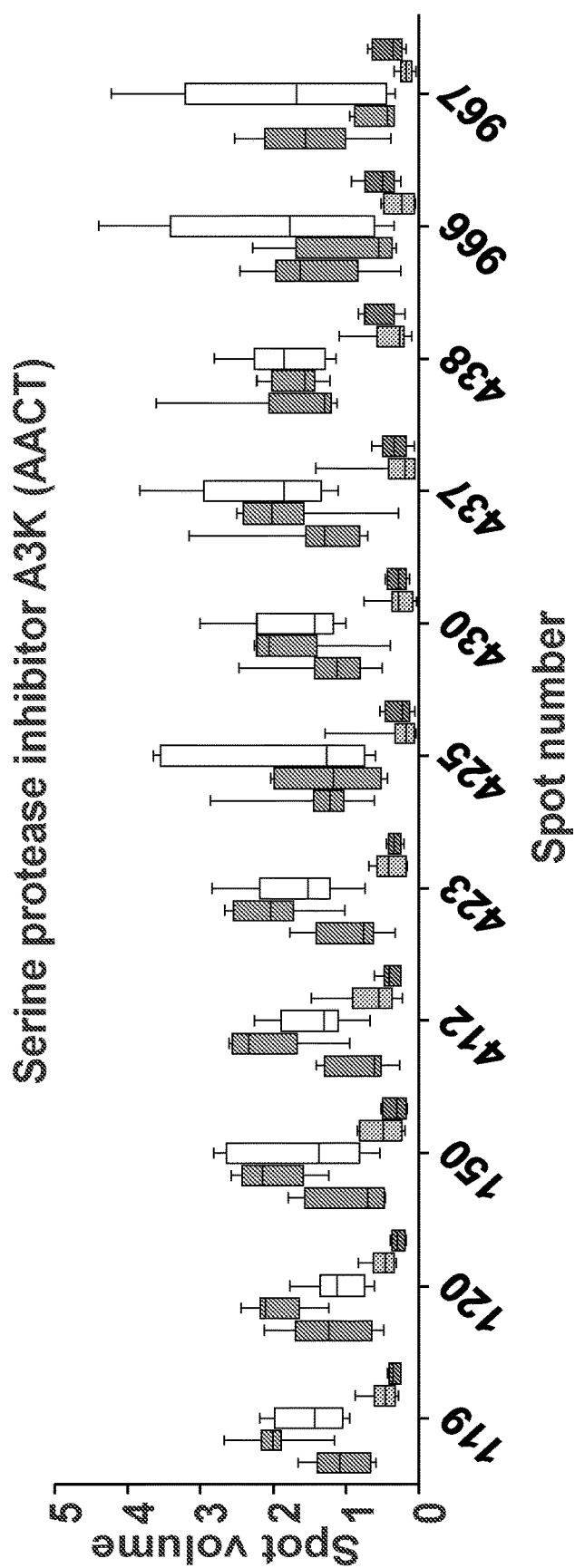

The positions of the eight proteins on a representative 2D DIGE overlay gel is given in FIG. 5A. Visual inspection of the box-and-whisker plots of the associated spot volumes demonstrated that each was specifically regulated in the GC versus non-GC phenotype (FF/FFIL6 versus WT/IL6/FFStat3) (FIG. 5B).

Verification of Candidate GC Biomarkers in Mouse Sera

Figure 6A:
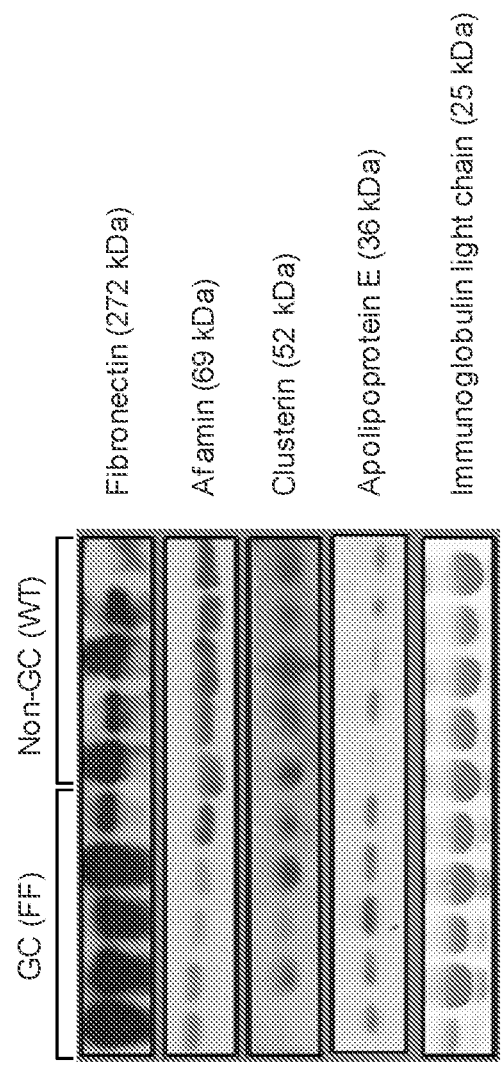
FIGS. 6A-6D—(FIG. 6A) Western blot detection of four candidate biomarkers identified in Example 1 in serum of GC mice (FF genotype, n=5) and non-GC (WT, n=5) mice. The immunoglobulin light chain was used as an input control for densitometric analysis.
Figure 6B:
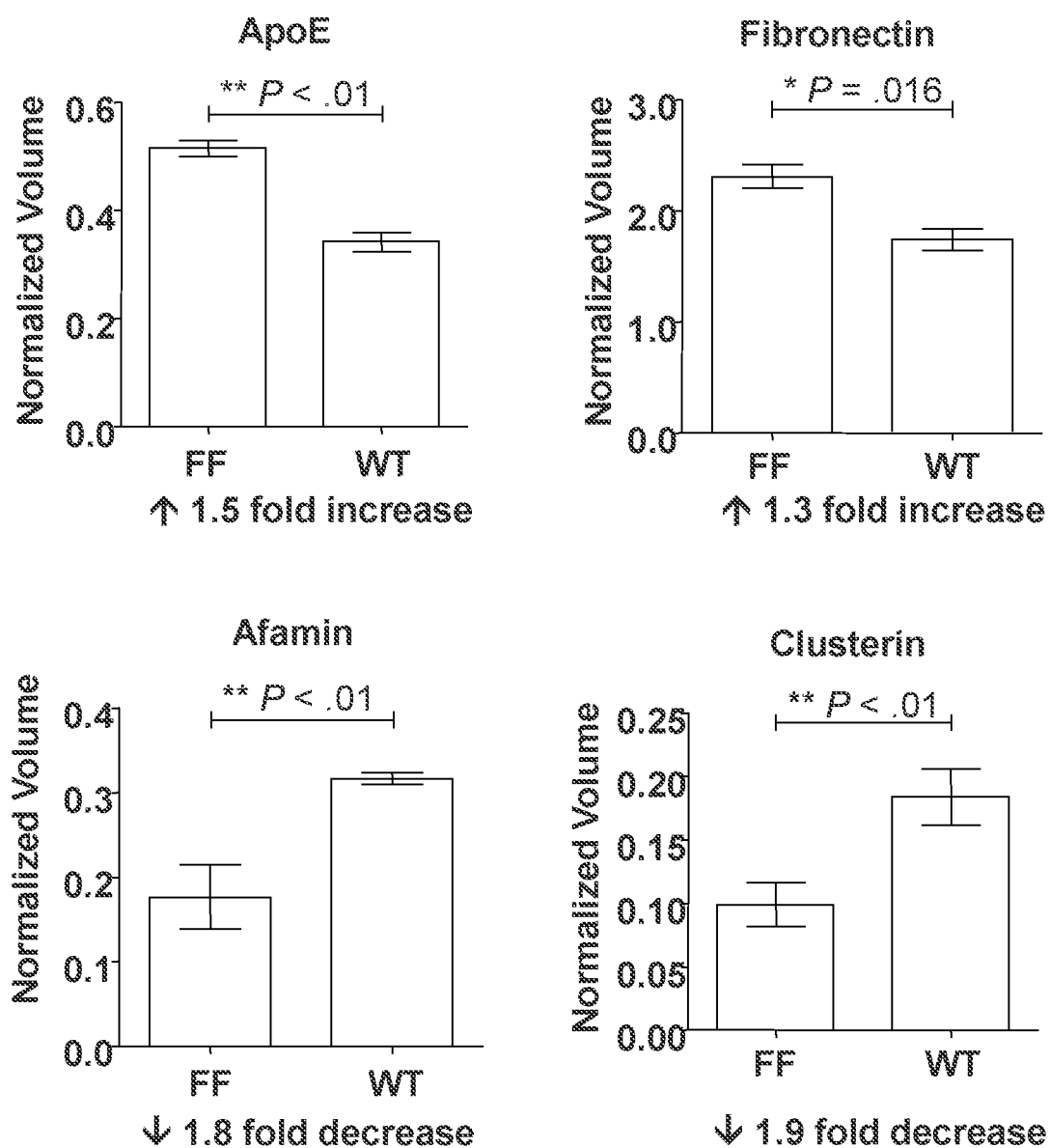

The regulation of total protein levels of afamin, apoE, clusterin and fibronectin in GC relative to non-GC mouse serum was verified by Western blotting using sera from five WT and five FF genotype mice. All four proteins were successfully detected (FIG. 6A) and quantified (FIG. 6B) relative to the immunoglobulin light chain. The serum levels of both apoE (P<0.01) and fibronectin (P=0.016) were found to be significantly elevated in the FF versus the WT mice, while afamin (P<0.01) and clusterin (P<0.01) were significantly down-regulated. The results obtained by Western blotting supported the 2D DIGE data in terms of direction of regulation in the GC relative to the non-GC phenotype.

Validation of Candidate GC Biomarkers in Human Sera

Figure 6C:
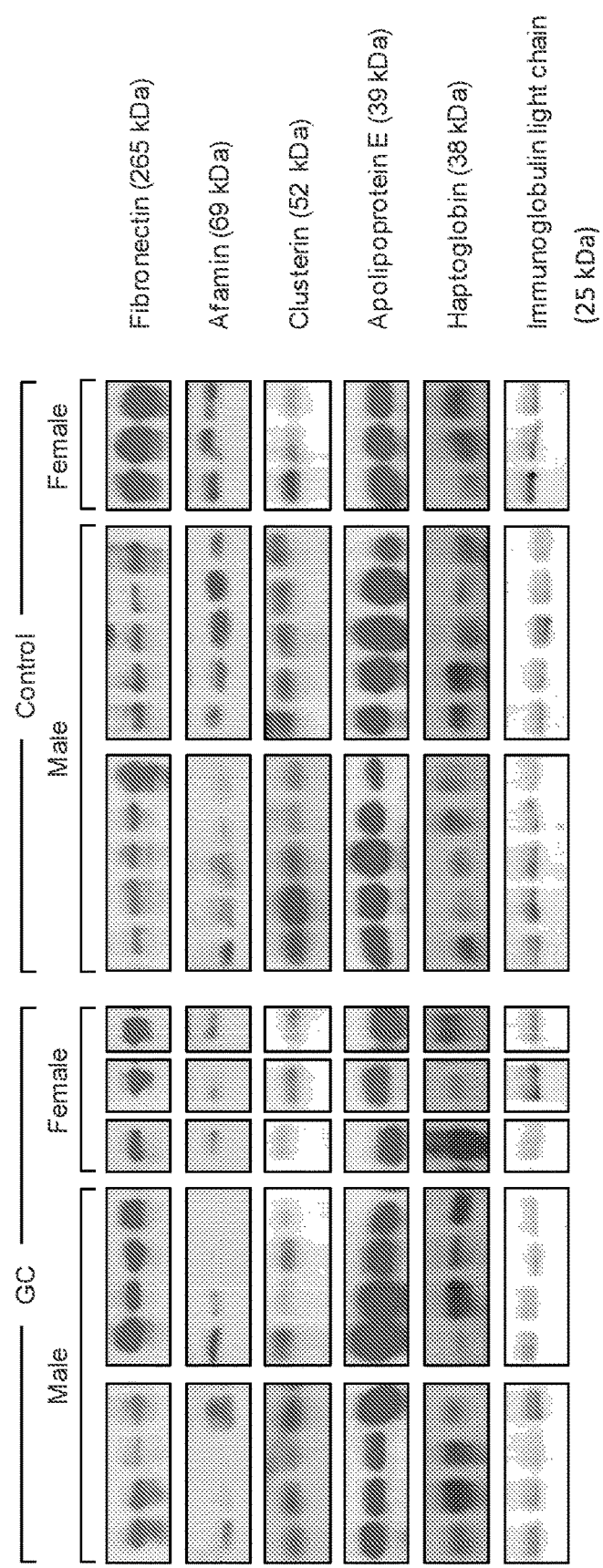

The regulation of total protein levels of afamin, apoE, clusterin, fibronectin and haptoglobin were investigated in human sera using samples from 11 preoperative GC patients and 13 healthy controls. All five proteins were successfully detected and quantified by Western blotting (FIG. 6C).

Figure 6D:
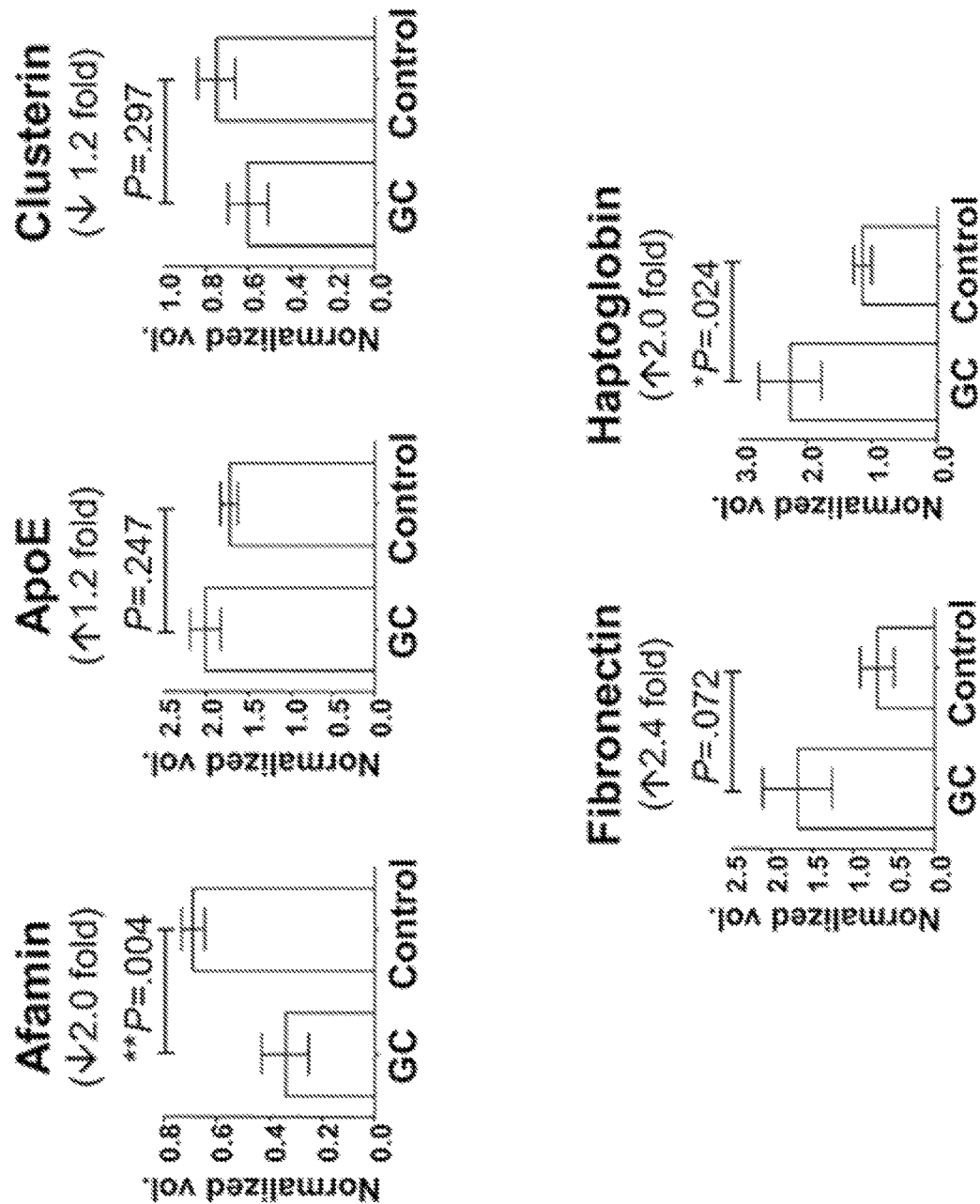

Densitometric analysis of GC patient versus controls (FIG. 6D) revealed that each protein demonstrated the expected direction of change observed in the GEM model whereby apoE, fibronectin and haptoglobin showed increased levels of expression, while afamin and clusterin showed decreased levels of expression. The expression levels were significantly different between GC patient and control sera for afamin (P=0.004) and haptoglobin (P=0.024) (FIG. 6D).

TABLE 3

| | | MS Parameters | | | | | | | | |
|---|---|---|---|---|---|---|---|---|---|---|
| Protein Uniprot ID Acc. number | Spot[a] | MOWSE score (cut off) | Matched queries | emPAI score | % seq. cover | Observed pI | Observed MW | Predicted pI[b] | Predicted MW[b] | Human homologue Uniprot ID Accession number |
| Afamin AFAM_MOUSE O89020 | 628 | 668 (34) | 24 | 1.46 | 38% | 4.68 | 94,100 | 5.54 | 69,379 | Afamin AFAM_HUMAN P43652 |
| | 631 | 911 (34) | 22 | 1.35 | 38% | 4.72 | 93,700 | | | |
| | 634 | 719 (35) | 21 | 1.15 | 29% | 4.76 | 93,600 | | | |
| | 637 | 394 (35) | 17 | 0.97 | 26% | 4.83 | 93,600 | | | |
| | 667 | 878 (34) | 23 | 1.46 | 38% | 4.87 | 90,500 | | | |
| | 668 | 841 (34) | 20 | 1.25 | 38% | 4.93 | 90,500 | | | |
| | 689 | 380 (34) | 10 | 0.43 | 19% | 4.74 | 88,500 | | | |
| Apolipoprotein E APOE_MOUSE P08226 | 1330 | 588 (35) | 16 | 2.16 | 39% | 5.37 | 31,000 | 5.56 | 35,867 | Apolipoprotein E APOE_HUMAN P02649 |
| | 1332 | 787 (35) | 25 | 4.37 | 41% | 5.51 | 31,000 | | | |
| Clusterin CLUS_MOUSE Q06890 | 1233 | 279 (34) | 5 | 0.36 | 12% | 4.12 | 39,100 | 5.46 | 51,656 | Clusterin CLUS_HUMAN P10909 |
| Fibronectin FINC_MOUSE P11276 | 121 | 2364 (34) | 53 | 0.74 | 28% | 5.31 | 174,600 | 5.39 | 272,489 | Fibronectin FINC_HUMAN P02751-7 |
| | 123 | 1875 (33) | 66 | 1.02 | 32% | 5.37 | 174,500 | | | |
| | 126 | 1895 (34) | 64 | 1.00 | 34% | 5.39 | 174,400 | | | |
| | 127 | 3017 (33) | 72 | 1.20 | 35% | 5.41 | 174,300 | | | |
| | 196 | 1258 (34) | 25 | 0.31 | 14% | 5.04 | 153,100 | | | |
| | 116 | 1846 (33) | 43 | 0.56 | 23% | 5.25 | 174,600 | | | |
| | 117 | 2244 (33) | 53 | 0.74 | 27% | 5.29 | 174,600 | | | |
| | 122 | 2505 (33) | 52 | 0.74 | 26% | 5.33 | 174,600 | | | |

To obtain more quantitative data using a clinically relevant analytical platform, the serum levels of afamin, apoE, haptoglobin, fibronectin and clusterin together with VDBP, IGFALS and AACT were measured by ELISA. In order to compare the relative sensitivities and specificities of the candidate biomarker proteins identified in this investigation to a currently implemented clinical marker, an ELISA for serum CA72-4 was also performed. Higher CA 72-4 levels have been associated with an increased risk of death by GC with evidence suggesting it is more prognostic and specific for GC than CEA and CA19-9 (Ucar E et al., 2008, *Adv. Ther.* 25: 1075-1084). The concentrations of the nine proteins were standardized by dividing each individual's result by the mean concentration of the protein in the control group. Accordingly, the mean concentrations of all proteins in the control group were 1. This facilitated a cross-candidate comparison of the markers on an equivalent scale (Faca V M et al., 2008, *PLoS Med.* 5:e123).

Figures 7A, 7B:
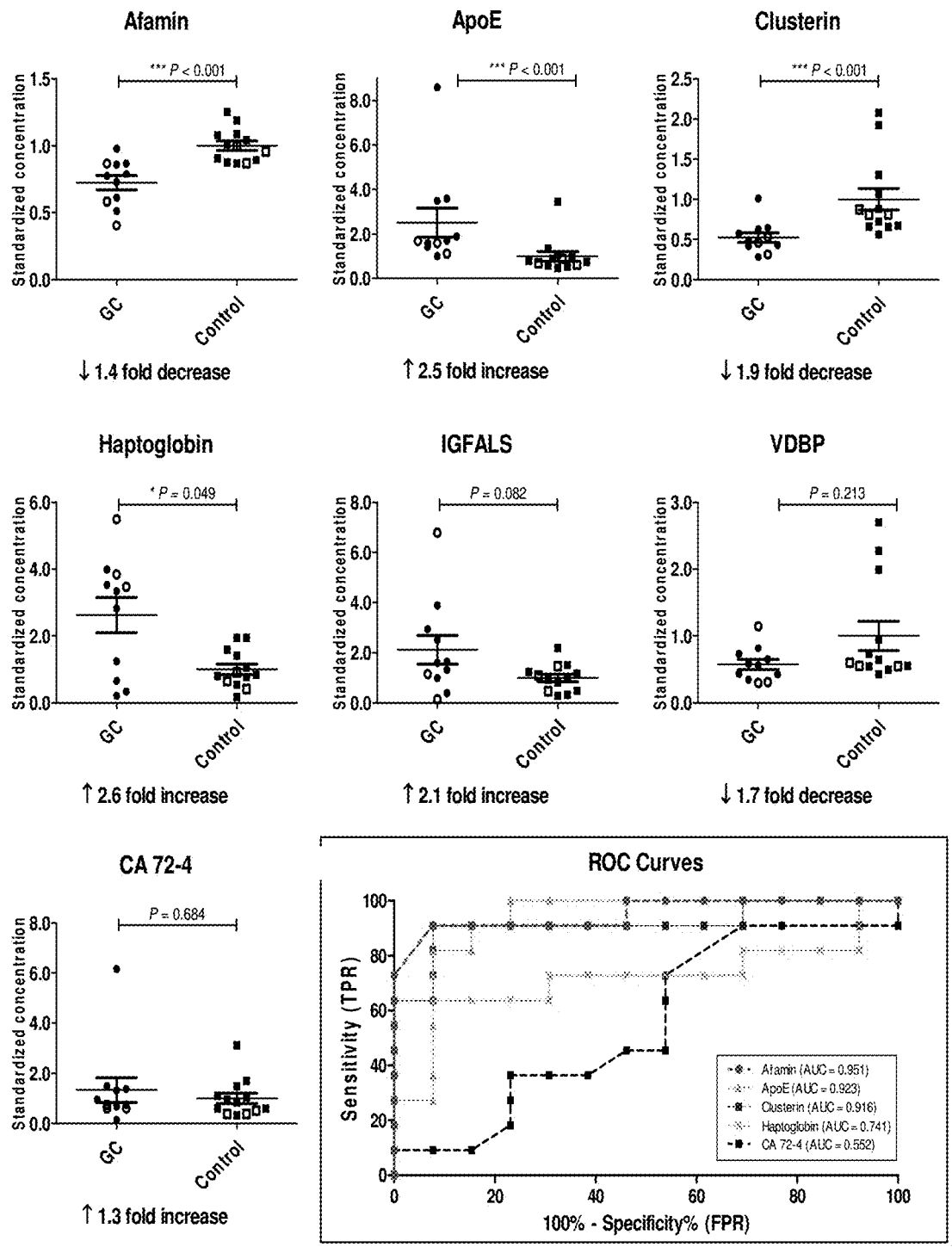
FIGS. 7A-7B—(FIG. 7A) Graphs showing the results of the seven ELISAs performed on GC patient (n=11) and control (n=13) serum in Example 1. P values were calculated using to the Mann-Whitney U test. Hollow data points are indicative of female subjects. Error bars represent the mean and standard error of the mean.
Figure 8:
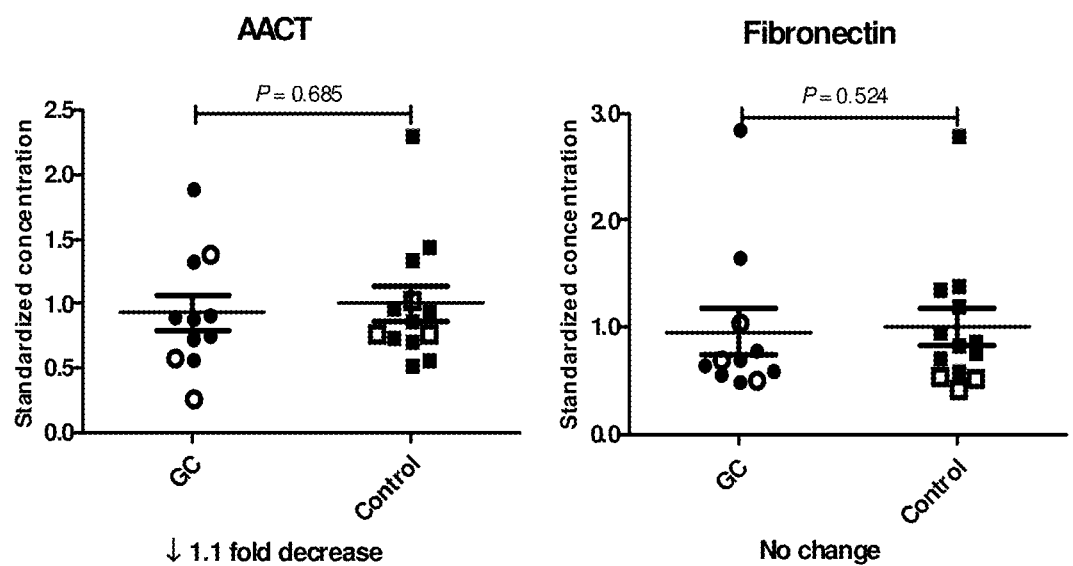
FIG. 8—Scatter plots depicting the ELISA results (standardized concentrations) for AACT and fibronectin in Example 1, which showed no apparent regulation between the GC patients and controls. P values were calculated using to the Mann-Whitney U test. Hollow data points are indicative of female subjects. Error bars represent the mean and standard error of the mean.

Serum concentrations of afamin, apoE, clusterin and haptoglobin were found to be significantly different between the GC patients and controls (P<0.05) (FIG. 7A). IGFALS and VDBP also showed differential expression between the groups based on the magnitude of fold change (P>0.05). CA72-4 was slightly elevated in the GC group with a non-significant 1.3 fold increase in expression (FIG. 7A). Scatter plots depicting the ELISA results for AACT and fibronectin, which showed no apparent regulation between the GC patients and controls (P>0.5), are provided in FIG. 8. Importantly, the direction of regulation observed in GC patient versus control sera for all candidates measured by Western blotting and/or ELISA (even those not demonstrating statistical significance) was congruent with the data obtained using 2D DIGE and Western blot analysis in the GEM model.

The diagnostic capabilities of the regulated proteins, afamin, apoE, clusterin, and haptoglobin, as well as CA 72-4 were further explored by ROC analysis (FIG. 7B). The sensitivities and specificities of afamin and clusterin were both 91% and 92%, respectively (both with 10/11 true positives, 12/13 true negatives). The sensitivity and specificity of apoE was 91% and 85%, respectively (10/11 true positives, 11/13 true negative), while for haptoglobin the sensitivity was 64% with 100% specificity (7/11 true positives, 13/13 true negatives). In contrast, the sensitivity and specificity of CA72-4 was only 36% and 77%, respectively (4/11 true positive, 10/13 true negatives).

Discussion

Currently, there is a deficit of sensitive and specific biomarkers for GC detection prior to targeted endoscopic diagnosis. In this Example, a biomarker discovery strategy was developed based on (i) the employment of a highly predictable and clinically relevant mouse model of human disease; (ii) a state-of-the-art proteomics approach for candidate biomarker identification; and (iii) the translation of the identified candidate biomarkers in human samples using a well characterised diagnostic platform, the ELISA.

Genetically inbred mice that recapitulate many critical features of human cancer are an attractive source of biomarkers given their virtual elimination of environmental and genetic variability. Recent attempts to utilize homogenous GEM models have yielded candidate biomarkers that have subsequently undergone successful orthogonal validation in human tissues for pancreatic, colon, breast, ovarian, hepatocellular, prostate and lung cancers (Faca V M et al., supra; Hung K E et al., 2009, *Cancer Prev. Res.* (*Phila.*), 2: 224-233; Pitteri S J et al., 2008, *J. Proteome Res.* 7:1481-1489; Pitteri S J et al., 2009, *PLoS One*, 4: e7916; Ritorto M S et al., 2011, *J. Proteome Res.* 10: 3012-3030; Cima I et al., 2011, *Proc. Natl. Acad. Sci. USA*, 108: 3342-3347; and Taguchi A et al., 2011, *Cancer Cell.* 20: 289-299).

Efforts to identify GC biomarkers in mice have largely been conducted using nude xenotransplantation mouse (XM) models injected with human GC cell lines. The expression levels of several proteins identified in this manner, including apoA1 and inter-alpha-trypsin inhibitor heavy chain H3 (ITIH3), have been corroborated in human plasma (Chong P K et al., 2010, *J. Proteome Res.* 9: 3671-3679; and Juan H F et al., 2004, *Proteomics*, 4: 2766-2775). Questions, however, remain regarding the appropriate treatment of control groups in such models and how GC-specific protein changes can be extrapolated from the ubiquitous acute phase response. Such concerns have been addressed here with the involvement of mice representing multiple mutant genotypes including FFIL6 mice that develop gastric tumours in the absences of systemic inflammation. Accordingly, these mice provide the genetic means to identify and verify proteomic changes associated with gastric tumourigenesis and the systemic acute phase response elicited by both IL-6 and IL-11. In addition, this study provides further evidence for the on-going use of GEM models in cancer research whereby all proteins identified here in the mouse were validated in human sera with the expected direction of fold-change using two different platforms (Western blotting and ELISA).

Proteomics analyses of MARS-depleted GEM sera by 2D DIGE led to the identification of the 31 differentially expressed murine proteins, corresponding to 28 human homologues. A subset of eight proteins followed up in verification and validation experiments. Generally, the observed molecular weights and isoelectric points of the eight mouse proteins on the 2D DIGE gels were larger and more acidic, respectively, than the predicted values based on the amino acid sequences as shown in Table 3. This indicated that these proteins may have been post-translationally modified. The UniProt entries of the mouse proteins revealed that seven of the eight contained potential N-linked glycosylation sequons with many sites known to be glycosylated. The single exception in the mouse was apoE, although the UniProt entry of human apoE indicates that it is modified by both N-linked and O-linked glycans.

Circulating serum glycoproteins are a promising source of cancer biomarkers. Changes in both protein expression and carbohydrate structure have been recognized as early hallmarks of cancer with glycoproteins playing an important role in tumour invasion and metastasis. Indeed, the current clinical marker CA 72-4 is a glycoprotein. The sensitivity and specificity values obtained by ROC analysis here for CA 72-4 (36% sensitivity, 77% specificity) were slightly lower than those described in the literature (40% sensitivity, >95% specificity). This, however, may be a reflection of the small size of the dataset herein and/or the particular ELISA that was employed. Nevertheless, using the same patient and control samples, the results obtained for afamin, IGFALS, VDBP, clusterin, and haptoglobin showed more accurate segregation of the GC patients from the controls in comparison with CA72-4. Furthermore, the individual sensitivities and specificities of afamin and clusterin were higher than the values reported for gastric photofluorography, the gold-standard screening test used in Japan. Therefore, six of the biomarkers identified in this Example (namely afamin, IGFALS, VDBP, clusterin, apoE and haptoglobin) provide an effective means to discriminate GC patients and healthy individuals. Furthermore, the diagnostic utility of these biomarkers may be improved though their combination in a multianalyte assay.

Example 2

Validation in Additional Gastric Cancer Patients

The results referred to in Example 1 above were further validated in a second cohort of gastric cancer patients (25 in total). In this experiment, blood was collected from both the male and female patients at the time of surgery and their sera stored at −80° C. until required for enzyme-linked immunosorbent assays (ELISAs). The cancers of the patients included a combination of five early (T1) and twenty late (T4) histological sub-types. A total of ten control samples were included for this experiment with blood being collected from the healthy volunteers by an experienced phlebotomist. Sera from control blood were also stored at −80° C. until required for ELISAs. As for Example 1, all experiments were approved by ethics committees of the Peter MacCallum Cancer Research Institute and the University of Adelaide.

Sandwich ELISA kits for the afamin, clusterin, haptoglobin, IGFALS and VDBP proteins were obtained from a single commercial supplier (Uscn Life Science Inc., Wuhan, China) to ensure consistency and assays were performed according to the manufacturer's instructions. In summary, collected serum was thawed and diluted with PBS, standards were prepared, and all samples were added in duplicate to 96-well microtitre plates coated with appropriate antibody for the specific proteins of interest. Next, avidin conjugated to Horseradish Peroxidase (HRP) was added to each well and incubated. Following this, TMB substrate was added, resulting in only those wells containing the specific protein, bio-conjugated antibody, and enzyme conjugated avidin, exhibiting a change in color. Subsequently, the reaction was terminated with the addition of sulphuric acid and the color change measured spectrophotometrically at 450 nm. The concentration of the specific protein was then determined by comparing the optical density of the samples to the standard curve. The optical density of standards was plotted against the known concentration of the standards on a log-log graph using Graphpad Prism and unknown concentrations interpolated from this. As described in Example 1, the concentrations of the five proteins were standardized/normalized by dividing the result for each test sample by the mean concentration of the protein in the control group. Accordingly, the mean concentrations of all proteins in the control group were 1. This facilitated a cross-candidate comparison of the markers on an equivalent scale.

Figure 9:
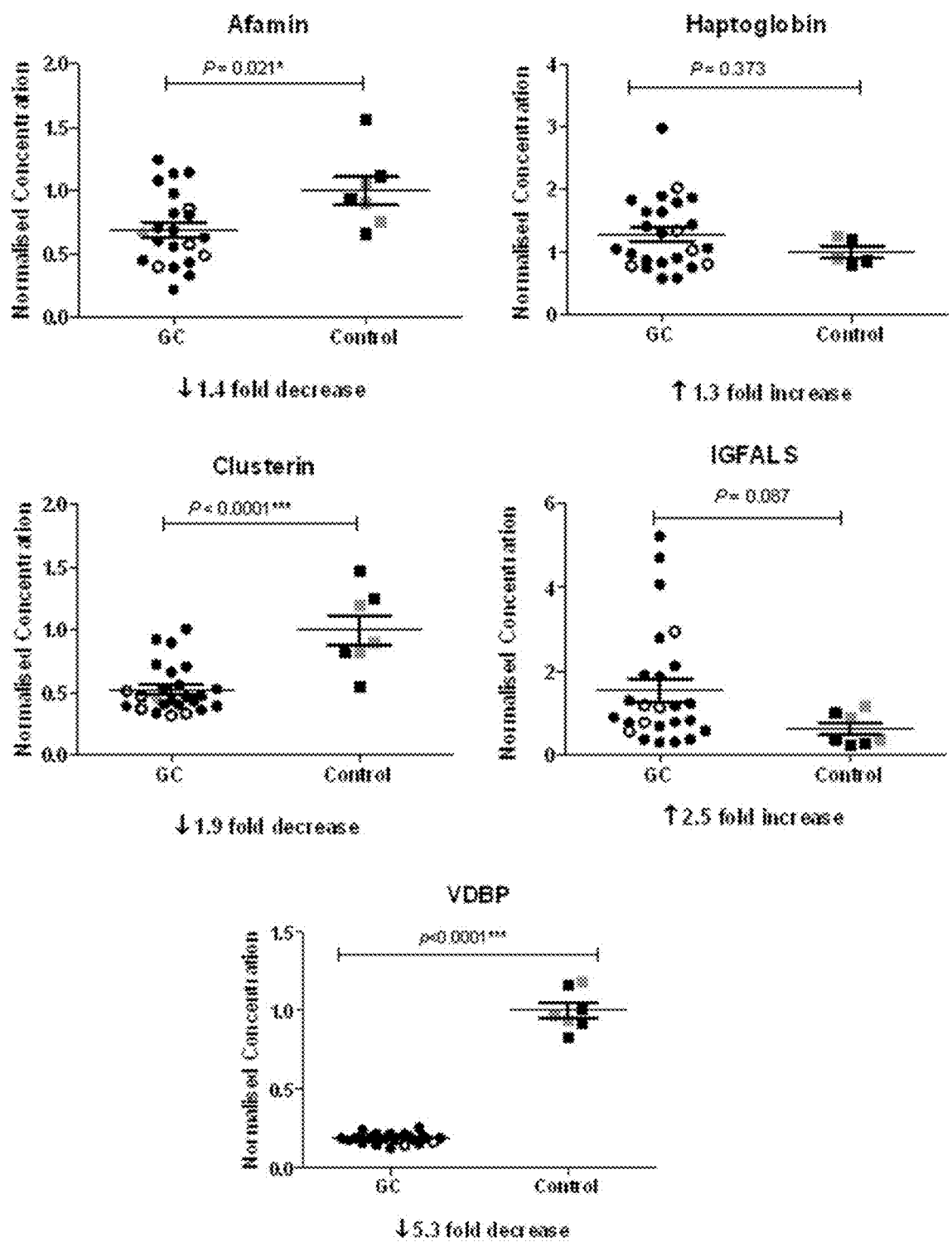
FIG. 9—Graphs showing the results of the five ELISAs performed on gastric cancer (GC) patient (n=25) and control (n=10) serum in Example 2. P values were calculated using to the Mann-Whitney U test. GC serum represented by dots, control serum represented by squares. Shaded symbols indicate female, black symbols indicate male. Unfilled circles indicate early stage GC and filled circles indicate late stage GC. Fold-changes in protein levels are represented on the x-axis and indicate regulation from control to GC.
Figure 10:
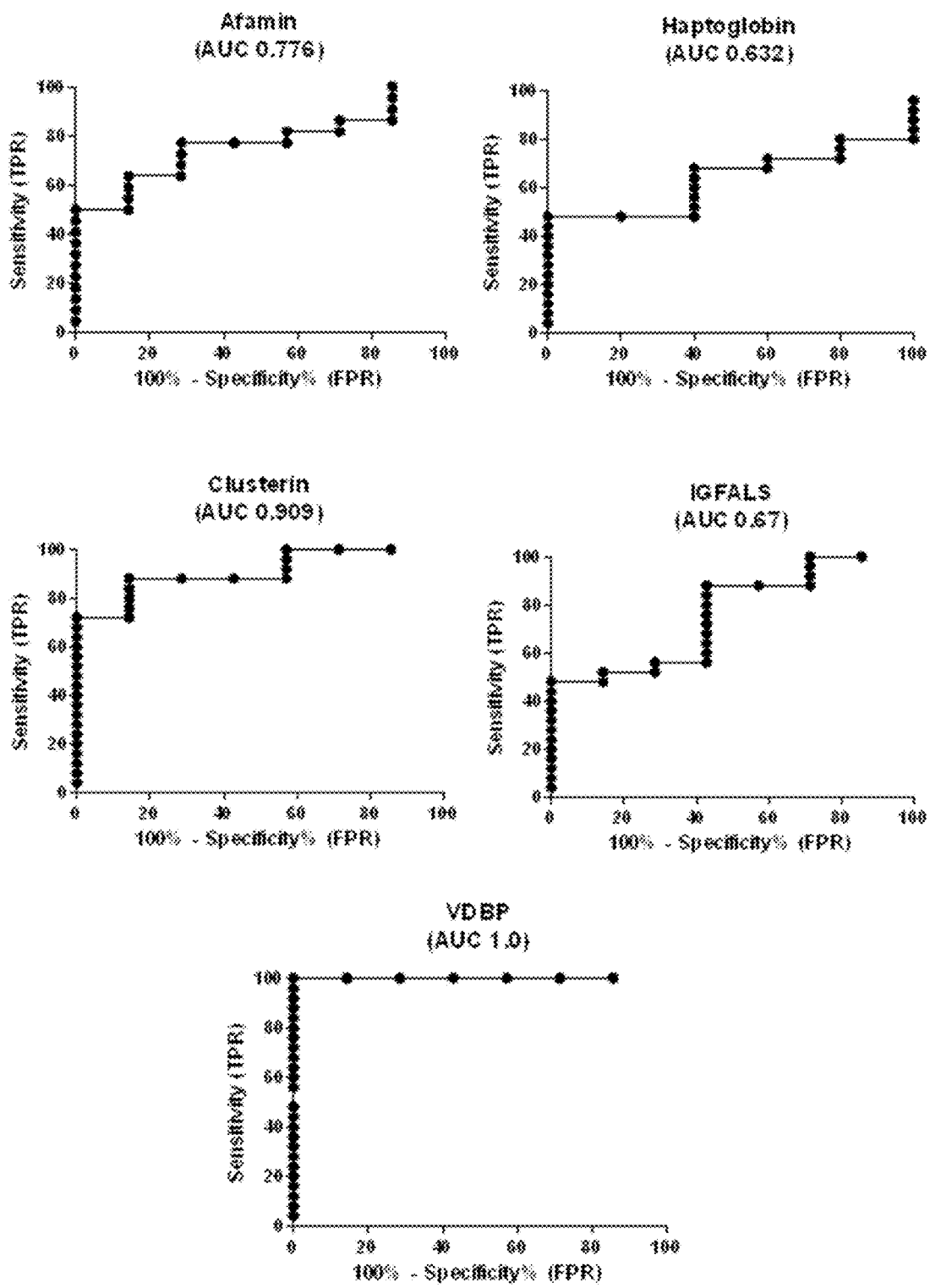
FIG. 10—ROC curves obtained for each of the five proteins analysed in Example 2 indicating sensitivity (true positive rate—TPR), specificity (false positive rate—FPR), and Area Under the Curve (AUC).

From the interpolated results, individual graphs were prepared for each protein (±SE) comparing results from gastric cancer (GC) serum samples and control serum samples. Results are shown in FIG. 9 and summarised in Table 4. ROC curves were subsequently created for each protein as shown in FIG. 10, and ROC curves for a combination of the proteins are shown in FIG. 11 (secondary combinations) and FIG. 12 (tertiary combinations).

TABLE 4

| Protein | Fold Change | Significance |
| --- | --- | --- |
| Afamin | −1.4* | 0.021 |
| Clusterin | −1.9*** | <0.0001 |
| IGFALS | +2.5 | 0.087 |
| VDBP | +5.3*** | <0.0001 |
| Haptoglobin | +1.3 | 0.373 |

The aim of this study was to confirm the suitability of afamin, clusterin, haptoglobin, IGFALS and VDBP (as shown in Example 1) to represent a suite of biomarkers for detection of gastric cancer. Building on from the ELISA results of Example 1, analysis of a new cohort of patients was conducted using ELISA kits from one manufacturer, thereby providing consistency throughout analysis of the proteins.

Differential regulation for each of the five proteins was consistent with the results of Example 1, with serum from gastric cancer patients having lower concentrations of afamin (p=0.021), clusterin (p<0.0001) and VDBP (p<0.0001), and higher concentrations of haptoglobin (p=0.373) and IGFALS (p=0.087) compared with the concentration of these proteins in serum from healthy controls (FIG. 9).

The second aim of this study was also to determine whether these five biomarkers could be used to identify early stage GC. Serum from early stage (T1) gastric cancer patients is difficult to obtain due to the pathology of the disease, and these samples (n=5) showed no separation from the late stage (T4) gastric cancer samples (n=20). This is of particular interest given that detection of tumours at an early stage enables early treatment leading to better patient outcomes.

Receiver Operating Condition (ROC) curves showing the sensitivity and specificity of each protein to distinguish true positive from false positive readings (FIG. 10) show VDBP, clusterin and IGFALS to be of particular interest individually. FIG. 11 shows secondary combinations of ROC curves for haptoglobin and VDBP, IGFALS and VDBP, IGFALS and afamin, clusterin and afamin, and VDBP and afamin. These pairings are of particular note for their potential for increasing the true positive rate and reducing the false positive rate for any diagnostic developed using this suite of proteins. The tertiary combinations shown in the ROC curves of FIG. 12 also provide evidence of the ability of combinations of these proteins to increase the true positive rate and reduce the false positive rate for any diagnostic developed.

The invention claimed is:

1. A method of treating gastric cancer in a subject, comprising:
    (a) obtaining a serum sample from a subject;
    (b) detecting a decrease in expression of vitamin D binding protein (VDBP) in the serum sample compared to a reference expression level for VDBP; and
    (c) administering an effective amount of a chemotherapy or radiotherapy for gastric cancer to the subject when a decrease in expression of VDBP is detected.

2. The method according to claim 1, wherein the expression of VDBP is detected by measuring the level of VDBP protein in the serum sample.

3. The method according to claim 1, further comprising one or more of the following steps:
    (d) detecting a decrease in expression of clusterin in the serum sample compared to a reference expression level for clusterin;
    (e) detecting an increase in expression of insulin like growth factor binding protein complex acid labile subunit (IGFALS) in the serum sample compared to a reference expression level for IGFALS;
    (f) detecting a decrease in expression of afamin in the serum sample compared to a reference expression level for afamin;
    (g) detecting an increase in expression of ApoE in the serum sample compared to a reference expression level for ApoE;
    (h) detecting an increase in expression of haptoglobin in the serum sample compared to a reference expression level for haptoglobin; and
    (i) administering an effective amount of a chemotherapy or radiotherapy for gastric cancer to the subject when a decrease in expression of clusterin is detected, an increase in expression of IGFALS is detected, a decrease in expression of afamin is detected, an increase in expression of ApoE is detected, or an increase in expression of haptoglobin is detected.

4. The method according to claim 3, wherein the expression of one or more of clusterin, IGFALS, afamin, ApoE and haptoglobin is detected by measuring the level of clusterin, IGFALS, afamin, ApoE and haptoglobin protein in the serum sample.

\* \* \* \* \*